(12) United States Patent
Sonesson et al.

(10) Patent No.: US 7,851,629 B2
(45) Date of Patent: Dec. 14, 2010

(54) DISUBSTITUTED PHENYLPIPERIDINES AS MODULATORS OF DOPAMINE AND SEROTONIN NEUROTRANSMISSION

(75) Inventors: Clas Sonesson, Billdal (SE); Lars Swanson, Öjersjö (SE); Nicholas Ross Waters, Göteborg (SE)

(73) Assignee: NSAB, Filial af Neurosearch Sweden AB, Sverige, Ballerup (DK)

( * ) Notice: Subject to any disclaimer, the term of this patent is extended or adjusted under 35 U.S.C. 154(b) by 0 days.

(21) Appl. No.: 11/567,925

(22) Filed: Dec. 7, 2006

(65) Prior Publication Data

US 2007/0179185 A1    Aug. 2, 2007

Related U.S. Application Data

(63) Continuation of application No. PCT/EP2005/006154, filed on Jun. 8, 2005.

(60) Provisional application No. 60/577,953, filed on Jun. 8, 2004, provisional application No. 60/637,530, filed on Dec. 20, 2004.

(30) Foreign Application Priority Data

Jun. 8, 2004 (SE) .................................... 0401464
Dec. 20, 2004 (SE) .................................... 0403142

(51) Int. Cl.
*C07D 211/08* (2006.01)
*A61K 31/445* (2006.01)
(52) U.S. Cl. ..................... 546/192; 514/317
(58) Field of Classification Search ................. 546/192; 514/317
See application file for complete search history.

(56) References Cited

U.S. PATENT DOCUMENTS

| 3,326,916 | A | | 6/1967 | Creighton et al. |
| 3,539,573 | A | * | 11/1970 | Hunziker et al. ............. 540/551 |
| 4,202,898 | A | | 5/1980 | Depoortere |
| 4,333,942 | A | * | 6/1982 | Eistetter et al. .............. 514/327 |
| 4,415,736 | A | | 11/1983 | Ciganek et al. |
| 4,504,660 | A | | 3/1985 | Klaubert et al. |
| 5,462,947 | A | | 10/1995 | Svensson et al. |
| 5,502,050 | A | | 3/1996 | Gross |
| 6,175,015 | B1 | | 1/2001 | Yuan et al. |
| 2003/0109532 | A1 | | 6/2003 | Sonesson et al. |
| 2007/0149542 | A1 | * | 6/2007 | Sonesson et al. ......... 514/254.1 |
| 2007/0270467 | A1 | * | 11/2007 | Sonesson et al. ............ 514/327 |

FOREIGN PATENT DOCUMENTS

| EP | 0060179 | 2/1982 |
| EP | 0369887 | 11/1989 |
| EP | 0094159 | 3/1990 |
| EP | 0533266 | 9/1992 |
| EP | 0533267 | 9/1992 |
| EP | 0533268 | 3/1993 |
| EP | 0659743 A1 * | 12/1993 |
| EP | 675118 | 4/1995 |
| FR | 1459013 | 5/1965 |
| GB | 850662 | 10/1957 |
| GB | 1560271 | 1/1977 |
| GB | 2078746 | 6/1981 |
| GB | 2083476 | 9/1981 |
| GB | 2027703 | 12/2006 |
| JP | 2000086603 A * | 3/2000 |
| NL | 6510107 | 2/1966 |
| WO | 8905799 | 6/1989 |
| WO | 9109594 | 7/1991 |
| WO | 9304684 | 12/1991 |
| WO | 9218475 | 10/1992 |
| WO | 9300313 | 1/1993 |
| WO | 9811068 | 3/1998 |
| WO | 0003713 | 1/2000 |
| WO | 0078728 | 12/2000 |
| WO | 0146144 | 6/2001 |
| WO | 0146145 | 6/2001 |
| WO | WO 01/46146 A1 * | 6/2001 |
| WO | WO 0146146 | 6/2001 |
| WO | 0205819 | 1/2002 |
| WO | 02059108 | 8/2002 |
| WO | 2004099150 | 11/2004 |
| WO | 2005019215 | 3/2005 |
| WO | 2005121087 | 12/2005 |
| WO | 2005121092 | 12/2005 |
| WO | 2006040156 | 4/2006 |
| WO | WO 2006/039325 A2 * | 4/2006 |
| WO | 2007042295 | 4/2007 |
| WO | 2007065655 | 6/2007 |

OTHER PUBLICATIONS

Bergel et al J. Chem. Soc. 1944, 261-265.*
Database Online: Chemical Abstracts Service, OH, XP002349551, Database accession No. 126:199585 compound with registry No. 187835-01-04 & Abstract WO 97/03986 A, Tanaka Hiroshi Kuroita, TA, Feb. 6, 1997.

(Continued)

*Primary Examiner*—Rita J Desai
*Assistant Examiner*—John Mabry
(74) *Attorney, Agent, or Firm*—Gauthier & Connors LLP

(57) ABSTRACT

The present invention relates to compounds which have therapeutic effects against disorders in the central nervous system, and in particular new 4-(ortho,meta-disubstituted phenyl)-1-alkypiperidines.

(1)

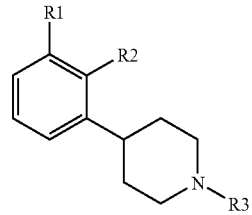

Figure 1:
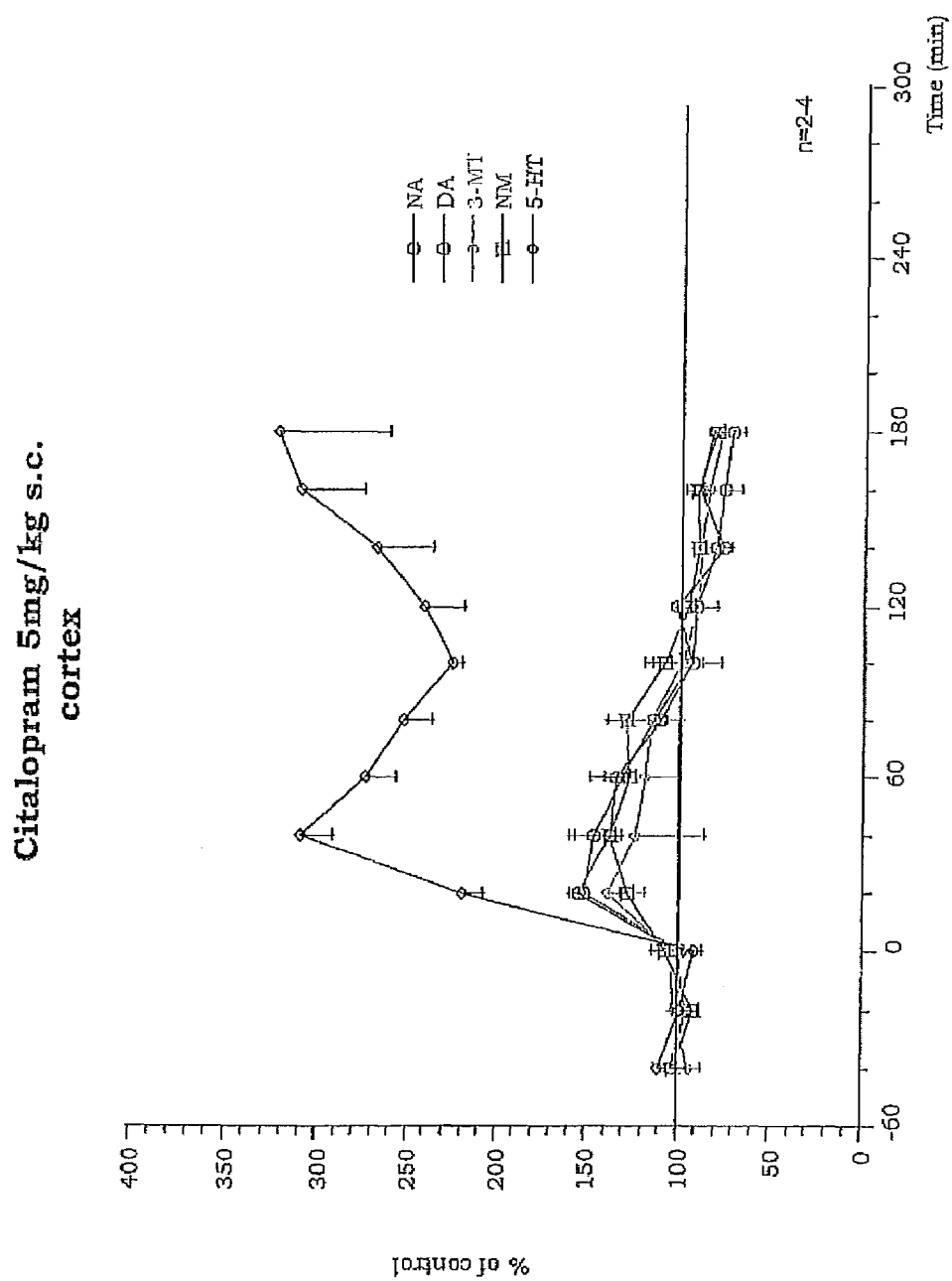
Figure 2:
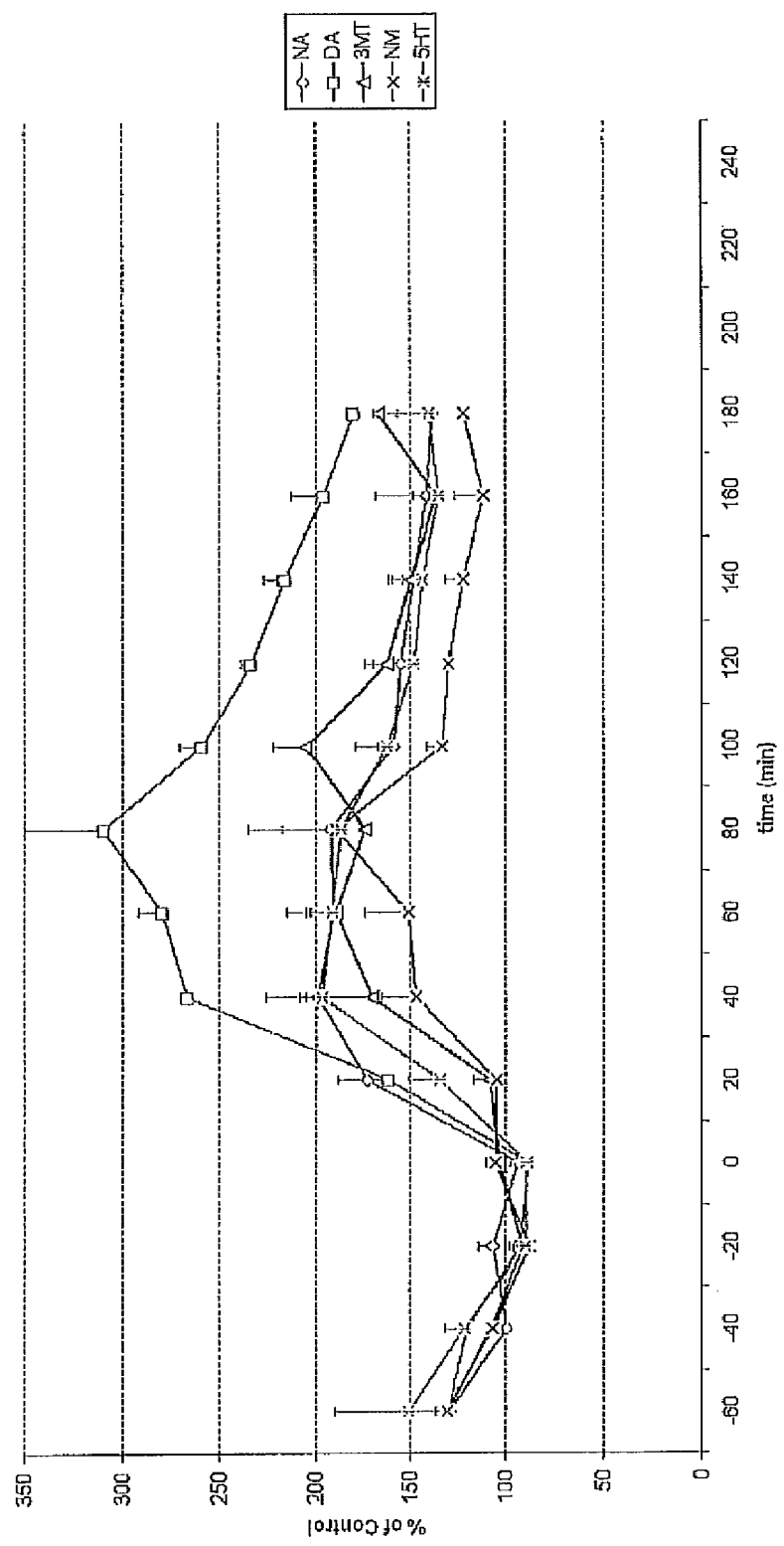
Figure 3:
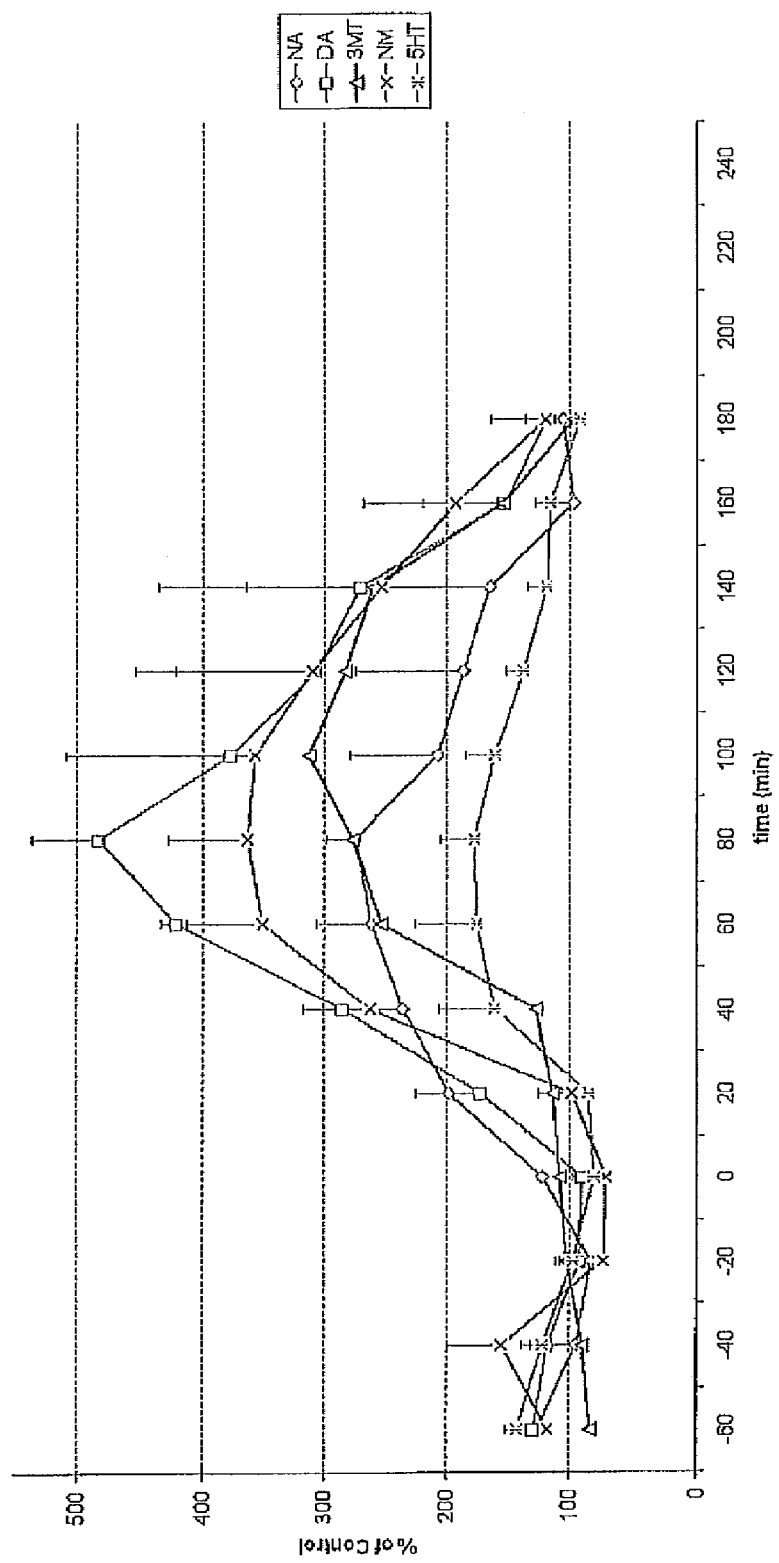
Figure 4:
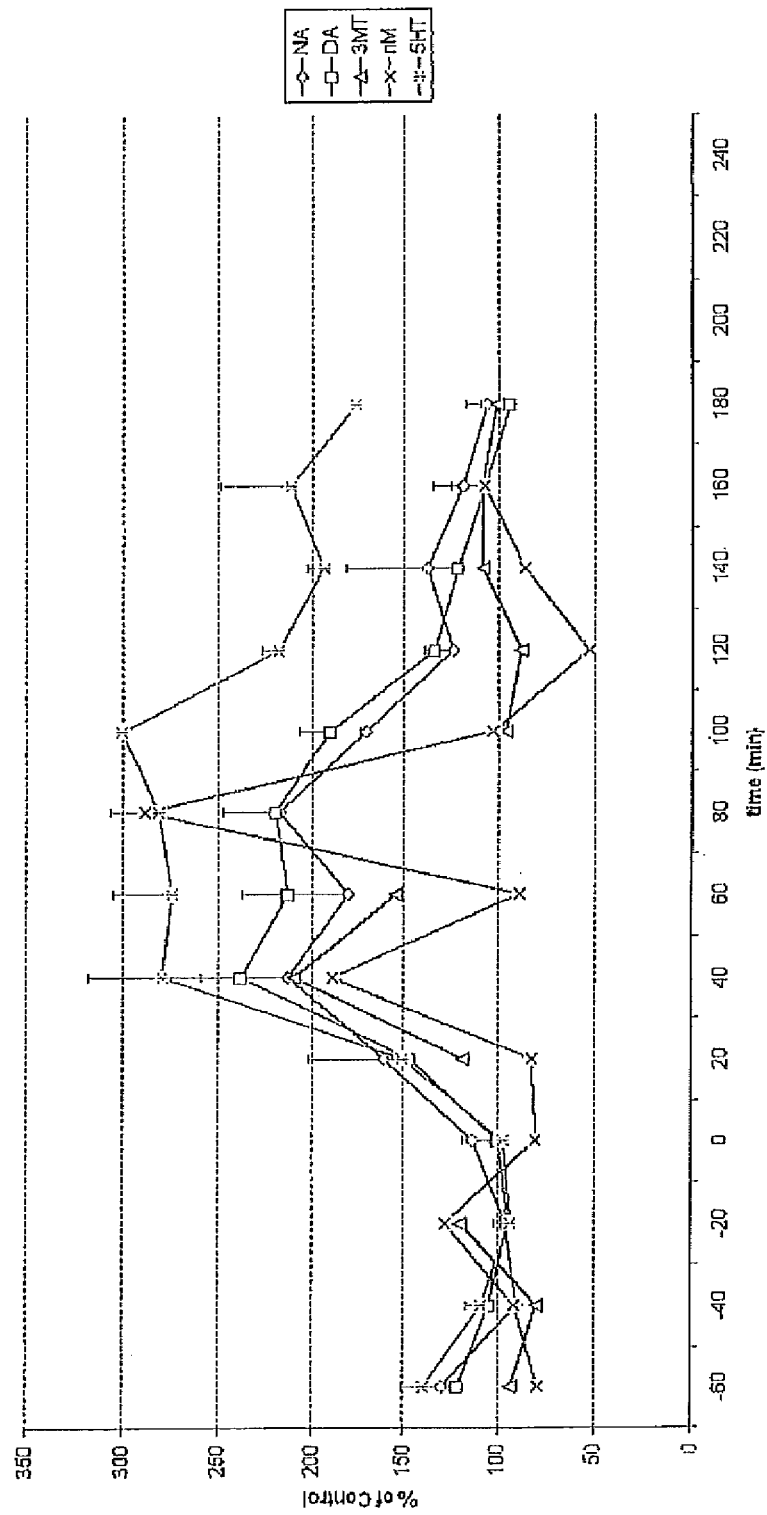

wherein R1, R2, and R3 are as defined.

8 Claims, 5 Drawing Sheets

OTHER PUBLICATIONS

Manoury et al., "Synthesis and Analgesic Activities of Some (4-Substituted phenyl-1-piperazinyl)alkyl 2-Aminobenzoates and 2-Aminonicotinates"; Journal of Medicinal Chemistry, 1979, vol. 22, No. 5; pp. 554-559.

Morita et al., "Practical Application of the Palladium-catalyzed Animation in Phenylpiperazine Synthesis: An Efficient Synthesis of a Metabolite of the Antipsychotic Agent Aripiprazole"; 1998 Elsevier Science Ltd., pp. 4811-4818.

Oshiro et al., "Novel Antipsychotic Agents with Dopamine Autoreceptor Agonist Properties: Synthesis and Pharmacology of 7-[4-(4-Phenyl-1-piperazinyl) butoxy]-3,4-dihydro-2(1H)-quinolinone Derivatives"; Journal of Medicinal Chemistry, 1998 American Chemical Society; pp. 658-667.

Smaill et al., "Mono-and difunctional nitrogen mustard analogues of the DNA minor groove binder pibenzimol. Synthesis, cytotoxicity and interaction with DNA"; Anti-Cancer Drug Design (1998), vol. 13, Oxford University Press; pp. 221-242.

Beugelmans et al., "Synthese d'heterocycles a 5 et 6 chainons par une strategie combinant des reactions SNAr et SRN1"; Institut de Chimie des Substances Naturelles, 1995 vol. 132; pp. 306-313.

Egawa et al., "A New Synthesis of 7H-Pyrido[1,2,3-de][1,4]benzoxazine Derivatives Including an Antibacterial Agent, Ofloxacin"; Research Labortories, Osaka, Japan; 1986 vol. 34, pp. 4098-4102.

Takai et al., "Reaction of Spiro[4H-3,1-benzoxazine-44'-piperidin]-2(1H)-one Derivatives and Related Compounds with Phosphorus Oxychloride"; Tokyo Research Laboratory, Tokyo, Japan; pp. 1901-1906, 1986.

Zhang et al., "Acta Pharmaceutica Sinica"; 1981; vol. 16, No. 6; pp. 414-424; Shanghai Institut of Pharmaceutical Industrial Research; Shanghai.

Klaubert et al., "N-(Aminophenyl)oxamic Acids and Esters as Potent, Orally Active Antiallergy Agents"; 1989 American Chemical Society; Research Fivision, Wyeth Laboratories Incc. Radnor, Pennsylvania; Journal of Medicinal Chemistry, vol. 24; pp. 742-748.

Self et al., "cine and tele Substitutions in the Reaction of 2,3-Dinitroaniline with Secondary Amines"; J.C.S. Chem. Comm., 1980; pp. 281-282.

Elslager et al., "Folate Antagonists. 3. 2,4-Diamino-6-(heterocyclic)quinazolines, a Novel Class of Antimetabolits with Potent Antimalarial and Antibacterial Activity"; Journal of Medicinal Chemistry; 1972, vol. 15, No. 8; pp. 827-836; Department of Chemistry, Research and Development Division, Ann Arobor, Michigan.

Berberian et al., "Comparison of Schistosomicidal Activity of Xanthenones and 4-Methyl-3-chloroanilines and Their Hydroxymethyl Analogs in Swiss Mice and Syrian Hamsters Infected with Schistosoma mansoni"; Sterlin-Winthrop Research Institute, Rensselaer, New York; pp. 607-610, 1969.

David W. Henry, "A Facile Synthesis of Piperazines from Primary Amines (1)"; Department of Pharmaceutical Chemistry, Stanford Research Institute; Dec. 1966; pp. 503-511.

Bergel et al., "Synthetic Analgesics, Part 1. Synthesis of Basic Benzofuran Derivatives and Certain 4-Phenylpiperidine Compounds"; 1944; pp. 261-265.

Nacci et al., "Antiblastic substances. L11. Tylophorine analogs. 1. Synthesis and cytostotic and cytotoxic activity of 4-(3,4-dimethoxphenyl)piperidine"; Farmaco Ed. Scintifica 1972, 328, (5) pp. 399-410.

Sonesson et al., "Substituted (S)-Phenylpiperidines and Rigid Congeners as Preferential Dopamine Autoreceptor Antagonists: Synthesis and Structure-Activity Relationships"; Journal of Medicinal Chemistry, 1994 American Chemical Society; pp. 2735-2752.

Radl et al., "Synthesis of Piperidine Analogs of 1-(3-Chlorophenyl)piperazine, a Well Known Serotonin Ligand"; Research Institute for Pharmacy and Biochemistry, Prague, Czech Republic; pp. 1017-1022, 1999.

Altomare et al., "Quantitative Structure-Metabolism Relationshiop Analyses fo MAO-Mediated Toxication of 1-Methyl-4-phenyl-1,2,3,6-tetrahydropyridine and Alalogues"; Chem. Res. Toxicol, 1992, vol. 5, pp. 366-375.

Carlsson et al., Interactions between glutamatergic and monoaminergic systems within the basal ganglia-implications for schizophrenia and Pakinson's disease; Department of Pharmacology, University of Goteborg, Goteborg, Sweden; 1990 Elsevier Science Publishers, vol. 13, No. 7, 1990; pp. 272-276.

Coyle et al., "Alzheimer's Disease: A Disorder of Cortical Cholinergic Innervation"; Science, vol. 219, Johns Hopkins School of Medicine, Baltimore, Maryland; pp. 1184-1190, 1983.

Grunblatt et al., "Potent neuroprotective and antioxidant activity of apomorphine in PMTP and 6-hydroxydopamine induced neurotoxicity"; Journal Neural transm. (1999) [Suppl] ; pp. 57-70.

Grunblatt et al., "Neuroprotective Strategies in Parkinson's Disease Using the Models of 6-Hydroxydopamine and MPTP"; Bruce Rappaport Family Research Institute and Department of Pharmacology, Haifa, Israel; pp. 262-273, 2000.

Philip G. Strange; "Antipsychotic Drugs: Importance of Dopamine Receptors for Mechanisms of Therapeutic Actions and Side Effects"; School of Animal and Microbial Sciences, Unitversity of Reading, Whiteknights, Reading, United Kingdom, vol. 53, No. 1; pp. 119-133, 2001.

Manfred E. Wolff; "Antipsychotic Agents, 4.1 Biologic Test Methods"; Burger's Medicinal Chemistry; 4th Edition, Part III; John Wiley & Sons; 1979, pp. 872-873.

Roth et al; "Biochemical Pharmacolog of Midbrain Dopamine Neurons"; Chapter 21; Yale University of Medicine, New Haven, CT; pp. 227 and 237, 1995.

Moore et al., "Dopaminergic Neuronal Systems in the Hypothalamus"; Department of Pharmacology and toxicology, Michigan State University, East Lansing, Michigan; Chapter 22; pp. 245 and 254, 1995.

Michel Le Moal., "Mesocorticolimbic Dopaminergic Neurons Functional and Regulatory Roles"; Universite de Bordeaux, Bordeaux, France; Chapter 25, pp. 283 and 292, 1995.

Philip Seeman., "Dopamine Receptors Clinical Correlates"; Departments of Pharmacology and Psychiatry, University of Toronto, Toronto, Ontario, Canada; Chapter 26, pp. 295-301, 1995.

George F. Koob; "Animal Models of Drug Addiction"; Department of Neuropharmacology, The Scripps Research Institute, La Jolla, California; Chapte 66; pp. 759 and 745-746 and 760, 1725 and 744, 1995.

Geyer et al., "Animal Models of Psychiatric Disorders"; Department of Neuropharmacology, The Scripps Research Institute, La Jolla, California; Chapter 68; pp. 787 and 793-795, 1995.

Paul Willner; "Dopaminergic Mechanisms in Depression and Mania"; Department of Psychology, University College of Swansea, Wales, United Kingdom; Chapter 80; pp. 921-928, 1995.

Bunney et al., "Schizophrenia and Glutamate"; Department of Pharmacology, University of Goteborg, Goteborg, Sweden; Chapter 101; pp. 1205 and 1207-1209, 1995.

Price et al., "Pharmacological Challenges in Anxiety Disorders"; University of Florida College of Medicine, Gainesville, Florida; Chapter 111; pp. 1311, 1317-1318 and 1320, 1995.

Amos D. Korczyn; "Parkinson's Disease"; Tel Aviv University, Rama Aviv, Israel; Chapter 126; pp. 1479-1482 , 1995.

George A. Bray; "Obesity, Fat Intake, and Chronic Disease"; Pennington Biomedical Researc Center, Louisiana State University, Baton Rouge, Louisiana; Chapter 137; pp. 1591 and 1600, 1995.

Katherine A. Halmi; "Basic Biological Overview of Eating Disorders"; Cornell Medical Center-Westchester Division, White Plains, New York; Chapter 138; pp. 1609-1610 and 1612, 1995.

Altomare et al., "Quantitative Structure-Metabolism Relationship Analyses fo MAO-Medicated Toxication of 1-Methyl-4-phenyl-1,2,3,6-tetrahydropyridine and Alalogues"; Chem. Res. Toxicol, 1992, vol. 5, pp. 366-375.

* cited by examiner

DISUBSTITUTED PHENYLPIPERIDINES AS MODULATORS OF DOPAMINE AND SEROTONIN NEUROTRANSMISSION

PRIORITY

The present invention is a continuation of PCT Application No. PCT/EP2005/006154 filed on Jun. 8, 2005, which claims priority to U.S. Provisional Applications 60/577,953, filed on Jun. 8, 2004, and 60/637,530, filed on Dec. 20, 2004, and Swedish Applications SE 0401464-3 filed Jun. 8, 2004 and SE 0403142-3 filed on Dec. 20, 2004, all of which are incorporated herein by reference in their entireties.

FIELD OF THE INVENTION

The present invention relates to new modulators of dopamine and serotonin neurotransmission, and more specifically to new 4-(ortho, meta disubstituted phenyl)-1-alkylpiperidines, and use thereof.

BACKGROUND OF THE INVENTION

Dopamine is a neurotransmitter in the brain. Since this discovery, made in the 1950s, the function of dopamine in the brain has been intensely explored. To date, it is well established that dopamine is essential in several aspects of brain function including motor, cognitive, sensory, emotional and autonomous functions (e.g. regulation of appetite, body temperature, sleep). Thus, modulation of dopaminergic function may be beneficial in the treatment of a wide range of disorders affecting brain functions. In fact, drugs that act, directly or indirectly at central dopamine receptors are commonly used in the treatment of neurological and psychiatric disorders, e.g. Parkinson's disease and schizophrenia. However, currently available dopaminergic pharmaceuticals can have severe side effects. For instance, dopamine antagonists are known to induce both motor (extrapyramidal side effects; EPS) and mental side effects (e.g. anhedonia, dysphoria, and impairment of cognition), and dopaminergic agonists are known to induce dyskinesias and psychoses (Goodman and Gilman's *The Pharmacological Basis of Therapeutics*, 9th ed./McGraw-Hill, USA. Chapter 18, p 407-416, Chapter 22, p 509-512, p 515-516). An approach adopted by many researchers to improve efficacy and reduce side effects of dopaminergic pharmaceuticals, is to develop novel dopamine receptor ligands with selectivity at specific dopamine receptor subtypes or with regional selectivity. Yet another class of compounds acting through the dopamine systems of the brain are dopaminergic stabilizers, which have shown to be useful in the treatment of both neurologic and psychiatric disorders (A. Ekesbo, PhD Thesis, Uppsala University, Sweden: Functional consequences of dopaminergic degeneration; clinical and experimental studies using a novel stabilizer of dopaminergic systems: Ekesbo et al, (−)-OSU6162 inhibits levodopa-induced dyskinesias in a monkey model of Parkinson's disease, *Neuroreport*, 8, 2567, 1997; Tedroff et al. Long-lasting improvement in motor function following (−)-OSU6162 in a patient with Huntington's disease. *Neurology*, 22; 53:1605-6, 1999; Gefvert O. et al, (−)-OSU6162 induces a rapid onset of antipsychotic effect after a single dose. A double-blind placebo-controlled pilot study. Scandinavian Society for Psychopharmacology, 41$^{st}$ Annual Meeting, Copenhagen Denmark *Nordic Journal of Psychiatry* 54/2 93-94, April 2000: Carlsson et al, *Annu. Rev. Pharmacol. Toxicol.*, 41, 237, 2001; Carlsson et al. *Current Medicinal Chemistry*, 11, 267, 2004).

Another dopaminergic compound, which has been referred to as a dopamine-serotonin system stabiliser, as well as a partial DA $D_2$ receptor agonist, is the recently-launched antipsychotic compound aripiprazole (Burris et al, *Pharm. Exp. Ther*, vol. 302, 381, 2002.). Furthermore, compounds referred to as dopaminergic stabilizers have been described in WO01/46145 WO01/46146, Pettersson et al. (The development of ACR16. A new class of dopaminergic stabilizers. Society for Neuroscience 32$^{nd}$ Annual Meeting, *Abstract 2002*, Vol. 28 part 1 1028, Orlando USA 2002) and Nyberg et al (Efficacy and tolerability of the new dopamine stabiliser ACR16 a randomised placebo-controlled add-on study in patients with schizophrenia 12th BIENNIAL WINTER WORKSHOP ON SCHIZOPHRENIA, 7-13 Feb. 2004, Davos, Switzerland.)

The typical pharmacological effects which are characteristic for dopaminergic stabilizers as described in WO01/46145, W001/46146 and Pettersson et al. 2002 can be summarised as: 1) Increased turnover of dopamine in the terminal areas of the ascending dopaminergic projections of the mammalian brain; 2) No or only weak behavioural effects in otherwise untreated rats; and 3) Inhibition of behavioural effects induced by psychostimulants or psychotomimetic compounds in the rat. In the present invention this is referred to as a dopaminergic stabilizer profile.

This invention relates to the field of treatment of mammals suffering from CNS disorders in which the symptoms can be affected by dopaminergic functions, where the treatment comprises administering to said mammal an amount of a new type of compound, with a dopaminergic stabilizer profile with additional effects on the serotonin neurotransmission.

DESCRIPTION OF PRIOR ART

Compounds belonging to the class of substituted 4-phenyl-N-alkyl piperidines and piperazines have been reported previously. Among these compounds, some are inactive in the CNS, some display serotonergic or mixed serotonergic/dopaminergic pharmacological profiles while some are full or partial dopamine receptor agonists or antagonists with high affinity for dopamine receptors.

Costall et al. *European J. Pharm.* 31, 94, (1975) and Mewshaw et al. *Bioorg. Med. Chem. Lett.*, 8,295, (1998) report compounds which are substituted 4-phenyl-piperazines, most of them being 2-, 3- or 4-OH phenyl substituted and displaying DA autoreceptor agonist properties. Fuller R. W. et al, *J. Pharmacol. Exp. Therapeut.* 218, 636, (1981) disclose substituted piperazines (e.g. 1-(m-trifluoro-methylphenyl)piperazine) which reportedly act as serotonin agonists and inhibit serotonin re-uptake. The comparative effects on the 5-hydroxyindole acetic acid concentration in rat brain by 1-(p-chlorophenol)-piperazine are disclosed by Fuller R. W. et al, *Res. Commun. Chem. Pathol. Pharmacol.* 29, 201, (1980). Fuller R. W. et al, *Res. Commun. Chem. Pathol. Pharmacol.* 17, 551, (1977) disclose the comparative effects on the 3,4-dihydroxy-phenylacetic acid concentration in rat brain by 1-(p-chlorophenol)-piperazine.

Boissier J. et al *Chem Abstr.* 61:10691c, disclose disubstituted piperazines. The compounds are reportedly adrenolytics, antihypertensives, potentiators of barbiturates, and depressants of the central nervous system.

A number of differently substituted piperazines have been published as ligands at 5-HT1A receptors, for example Glennon R. A. et al *J. Med. Chem.*, 31, 1968, (1988), Mokrosz, J. et al *Arch. Pharm.* (Weinheim) 328, 143-148 (1995), and van Steen B. J., *J. Med. Chem.*, 36, 2751, (1993), Dukat M.-L., *J. Med. Chem.*, 39, 4017, (1996).

GB2027703 discloses substituted phenyl piperazines as analgesics and psychotropic agents. GB1560271 discloses para-substituted meta-trifluoromethylphenyl piperazines and their therapeutic use in CNS and cardiovascular disorders. U.S. Pat. No. 4,202,898 discloses substituted phenylpiperazines for the treatment of anxiety and depression. U.S. Pat.

No. 3,326,916 discloses different N-alkyl substituted 4-(3-trifluoromethyl-phenyl)-piperazines for the treatment of anxiety and related psychiatric conditions. WO9811068 discloses substituted piperazines as selective dopamine D4 ligands to be used in the treatment of anxiety, depression, schizophrenia, obsessive ideas, Parkinson's disease, tardive dyskinesia, nausea and gastro-intestinal tract disorders.

A number of 4-phenylpiperidine derivatives are known. EP0369887 disclose substituted 4-(meta-trifluoromethylphenyl)-1,2,3,6-tetrahydropyridines for treatment of anxiety. WO00/03713 discloses a method for the treatment of schizophrenia and other dopamine system dysfunctions by using substituted 1-methyl-4-phenyl-1,2,3,6-tetrahydropyridines.

U.S. Pat. No. 4,415,736 discloses 4-(2,3-dimethoxy-phenyl)-1-methyl-4-piperidinol as a synthesis intermediate.

Glennon et al. (U.S. Pat. No. 6,057,371) claim a method for treating sigma receptor associated CNS disorder, comprising the adminstration of arylamines, including arylpiperidines, which are either unsubstituted or mono-substituted at the aryl ring. The compounds exhibit a high binding affinity with respect to the sigma receptor. WO 91/095954 states that the term "high affinity" is intended to mean a compound which exhibits an $IC_{50}$ of less than 100 nM in the assay against $^3$H-DTG described in Weber et al. *Proc. Natl. Acad. Sci.* (USA) 83: 8784-8788). Specifically, WO 91/095954 discloses compositions relating to "the discovery that certain phenylalkyl-amine, aminotetraline, piperazine, piperidine and related derivatives have high binding to the sigma receptor and unexpectedly low binding for the PCP and DA receptors" (see page 11, lines 33-36). WO 91/095954 and WO 93/00313 both require that the compounds have a high binding affinity to the sigma receptor and do not disclose that the compounds are pharmacologically active in the absence of sigma receptor affinity. In addition, clinical studies investigating the properties of sigma receptor ligands in schizophrenic patients have not generated evidence of antipsychotic activity, nor activity in any other CNS disorder. Two of the most extensively studied selective sigma receptor antagonists, BW234U (Rimcazole) and BMY14802, have both failed in clinical studies in schizophrenic patients (Borison et al, 1991, *Psychopharmacol Bull* 27(2): 103-106; Gewirtz et al, 1994, *Neuropsychopharmacology* 10:37-40).

In addition, it is known that compounds with formulae II (WO01/46145) and III (WO01/46146) possess dopaminergic stabilizer properties.

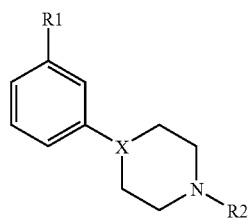

Formula II

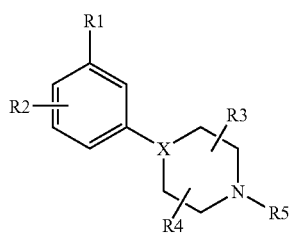

Formula III

In formula II;

X is, inter alia, CH, $R_1$ is selected from the group consisting of $OSO_2CF_3$, $OSO_2CH_3$, $SOR_3$, $SO_2R_3$, $COR_3$, CN, $NO_2$, $CONHR_3$, $CF_3$ (proviso X is CH or C) F, Cl, Br, I (wherein $R_3$ is as specified below);

$R_2$ is selected from the group consisting of $C_1$-$C_4$ alkyl, allyl, $CH_2SCH_3$, $CH_2CH_2OCH_3$, $CH_2CH_2CH_2F$, $CH_2CF_3$, 3,3,3-trifluoropropyl, 4,4,4-trifluorobutyl, or —$(CH_2)$—$R_4$ (wherein $R_4$ is as specified below);

$R_3$ is selected from the group consisting of $C_1$-$C_3$ alkyl, $CF_3$, or $N(R_2)_2$;

$R_4$ is selected from the group consisting of $C_3$-$C_6$ cycloalkyl, 2-tetrahydrofurane, 3-tetra-hydrofuran.

In formula III;

X is, inter alia, CH, $R_1$ is selected from the group consisting of $OSO_2CF_3$, $OSO_2CH_3$, $SOR_7$, $SO_2R_7$, $COR_7$, CN, $NO_2$, $CONHR_3$, $CF_3$, F, Cl, Br, I (wherein $R_3$ is as specified below), 3-thiophene, 2-thiophene, 3-furane, 2-furane;

$R_2$ is selected from the group consisting of F, Cl, Br, I, CN, $CF_3$, $CH_3$, $OCH_3$, OH, $NH_2$ $R_3$ and $R_4$ are independently H or $C_1$-$C_4$ alkyl $R_5$ is selected from the group consisting of $C_1$-$C_4$ alkyl, allyl, $CH_2SCH_3$, $CH_2CH_2OCH_3$, $CH_2CH_2CH_2F$, $CH_2CF_3$, 3,3,3-trifluoropropyl, 4,4,4-trifluorobutyl, or —$(CH_2)$—$R_6$;

$R_6$ is selected from the group consisting of $C_3$-$C_6$ cycloalkyl, 2-tetrahydrofurane, 3-tetra-hydrofurane.

$R_7$ is selected from the group consisting of $C_1$-$C_3$ alkyl, $CF_3$ or $N(R_4)_2$ However, WO01/46145 (Formula II) only discloses mono-substitution of the aryl ring, and does not exemplify ortho-substitution. WO01/46146 does not disclose 2,3-disubstitution of the aryl ring, and it can be seen that alternative substitution patterns (e.g. 3,4-disubstitution in which the 4-position is halogen) are not as potent as the 2,3-disubstitution disclosed in the present invention. In addition, there is no guidance in neither WO01/46146 nor WO01/46145 to obtain compounds with additional effects on the serotonin neurotransmission.

SUMMARY OF THE INVENTION

The object of the present invention is to provide new pharmaceutically active compounds, especially useful in treatment of disorders in the central nervous system, having increased potency as dopaminergic stabilizers and additional effect on serotonin neurotransmission.

The substances according to the present invention have been found in rat tests to act preferentially on dopaminergic systems in the brain. They have effects on biochemical indices in the brain with the characteristic features of dopamine antagonists. However, the substances according to the invention show no, or only limited, inhibitory effects on spontaneous locomotion over a wide dose range. Furthermore, the substances according to the invention can induce a slight behavioural activation, in particular when baseline locomotor activity is low. However, the substances in the present invention inhibit the behavioural activation induced by psychostimulants and psychotomimetics. In addition, the compounds of the present invention can increase the levels of serotonin in various brain regions including cortical regions.

DETAILED DESCRIPTION OF THE INVENTION

The present invention relates to new 4-(ortho, meta disubstituted phenyl)-1-alkylpiperidines in the form of free base or pharmaceutically acceptable salts thereof, pharmaceutical compositions containing said compounds and use of said compounds in therapy.

Specifically, the invention relates to a compound of Formula 1:

(1)

wherein:
  R$_1$ is selected from the group consisting of —CN, —OCF$_3$, —OCHF$_2$, —SCF$_3$, —SCHF$_2$, —CF$_3$, F, Cl, —CH$_3$ and —OCH$_3$;
  R$_2$ is selected from the group consisting of F, Cl, Br, and CH$_3$;
  R$_3$ is selected from the group consisting of C$_1$-C$_3$ alkyls and allyl, provided that when R$_1$ is CN or CF$_3$, R$_3$ can only be C$_1$-C$_2$ alkyls;
  and the pharmaceutically acceptable salts thereof.

As used herein the term C$_1$-C$_3$ alkyl refers to an alkyl group containing 1-3 carbon atoms. The various carbon moieties are defined as follows: alkyl refers to an aliphatic hydrocarbon radical such as methyl, ethyl and n-propyl. The term "allyl" refers to the group —CH$_2$—CH=CH$_2$ Inclusion of two substituents on the aryl ring of such compounds—one in the 2-position and the other in the 3-position—increases their potency in modulating dopamine neurotransmission. The unprecedented increase in potency of these 2,3-disubstituted compounds as compared to the mono-substituted, or the 3,4-disubstituted compounds, is illustrated in TABLE 1 and 3.

TABLE 1

Estimated ED$_{50}$ values for the increase in DOPAC (3,4-dihydroxyphenylacetic acid) in the rat striatum after systemic adminstration of test compound. For methods and statistical calculations see the enclosed tests.

| | ED$_{50}$ DOPAC μmol/kg |
|---|---|
| Examples | |
| Example 3 | 7.5* (6.0-9.9) |
| Example 2 | 24* (20-28) |
| Example 6 | 41* (32-54) |
| Example 11 | 26* (22-31) |
| Comparative Examples | |
| Example 9 of WO01/46146 | 40** (36-47) |
| Example 43 of WO01/46146 | 35** (27-44) |
| Claimed in WO01/46146 | 64** (50-81) |
| Example 6 of WO01/46145 | 81* (71-102) |

TABLE 1-continued

Estimated ED$_{50}$ values for the increase in DOPAC (3,4-dihydroxyphenylacetic acid) in the rat striatum after systemic adminstration of test compound. For methods and statistical calculations see the enclosed tests.

| | ED$_{50}$ DOPAC µmol/kg |
|---|---|
| 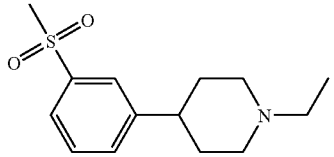<br>Example 12<br>of WO01/46145 | 154*<br>(121-198) |
| 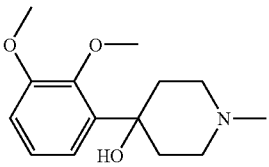<br>Example 1 and 2 in<br>U.S. Pat. No. 4,415,736 | n.d*** |

*in ED$_{50}$ estimates the maximal effects have been limited to 350-400% of control.
**in ED$_{50}$ estimates the maximal effects have been set to 200% of control (this is the maximal increase in DOPAC that is possible to achieve for these compounds).
***not determined.; The ED$_{50}$ value was not possible to calculate because the compound did not reach sufficient high DOPAC levels after administration of 100 µmol/kg.

One aim of the present invention is to provide new compounds for therapeutic use, and more precisely compounds for modulation of dopaminergic systems in the mammalian brain, including human brain.

Another aim of the invention is to provide compounds with therapeutic effects after oral administration.

In a first embodiment, the present invention relates to 4-(ortho, meta disubstituted phenyl)-1-alkylpiperidines:

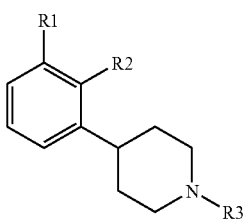

and pharmaceutically acceptable salts thereof, wherein $R_1$, $R_2$, $R_3$, are as defined above.

Within this group of compounds, $R_1$ is preferably selected from the group consisting of CN, $CF_3$, F and Cl. More preferably, $R_1$ is selected from the group consisting of F, Cl and $CF_3$.

In one embodiment, $R_2$ is selected from the group consisting of F and Cl. In another embodiment, $R_3$ is selected from the group consisting of methyl, ethyl and n-propyl (provided $R_1$ is not $CF_3$ or CN). Especially preferred compounds of the invention are those in which $R_2$ is F and $R_3$ is selected from the group consisting ethyl or n-propyl.

The preferred structures are:
4-(3-fluoro-2-methylphenyl)-1-propylpiperidine
1-ethyl-4-(3-fluoro-2-methylphenyl)piperidine
1-allyl-4-(3-fluoro-2-methylphenyl)piperidine
4-(2,3-difluorophenyl)-1-propylpiperidine
4-(2,3-difluorophenyl)-1-ethylpiperidine
1-allyl-4-(2,3-difluorophenyl)piperidine
4-(2-chloro-3-fluorophenyl)-1-propylpiperidine
4-(2-chloro-3-fluorophenyl)-1-ethylpiperidine
1-allyl-4-(2-chloro-3-fluorophenyl)piperidine
1-ethyl-4-[2-methyl-3-(trifluoromethyl)phenyl]piperidine
1-ethyl-4-[2-fluoro-3-(trifluoromethyl)phenyl]piperidine
4-[2-chloro-3-(trifluoromethyl)phenyl]-1-ethylpiperidine
4-(3-chloro-2-methylphenyl)-1-propylpiperidine
4-(3-chloro-2-methylphenyl)-1-ethylpiperidine
1-allyl-4-(3-chloro-2-methylphenyl) piperidine
4-(3-chloro-2-fluorophenyl)-1-propylpiperidine
4-(3-chloro-2-fluorophenyl)-1-ethylpiperidine
1-allyl-4-(3-chloro-2-fluorophenyl)piperidine
4-(2,3-dichlorophenyl)-1-propylpiperidine
4-(2,3-dichlorophenyl)-1-ethyl piperidine
1-allyl-4-(2,3-dichlorophenyl)piperidine
4-[3-(difluoromethoxy)-2-methylphenyl]-1-propylpiperidine
4-[3-(difluoromethoxy)-2-methylphenyl]-1-ethylpiperidine
1-allyl-4-[3-(difluoromethoxy)-2-methylphenyl]piperidine
4-[3-(difluoromethoxy)-2-fluorophenyl]-1-propylpiperidine
4-[3-(difluoromethoxy)-2-fluorophenyl]-1-ethylpiperidine
1-allyl-4-[3-(difluoromethoxy)-2-fluorophenyl]piperidine
4-[2-chloro-3-(difluoromethoxy)phenyl]-1-propylpiperidine
4-[2-chloro-3-(difluoromethoxy)phenyl]-1-ethylpiperidine
1-allyl-4-[2-chloro-3-(difluoromethoxy)phenyl]piperidine
4-[2-methyl-3-(trifluoromethoxy)phenyl]-1-propylpiperidine
1-ethyl-4-[2-methyl-3-(trifluoromethoxy)phenyl]piperidine
1-allyl-4-[2-methyl-3-(trifluoromethoxy)phenyl]piperidine
4-[2-fluoro-3-(trifluoromethoxy)phenyl]-1-propylpiperidine
1-ethyl-4-[2-fluoro-3-(trifluoromethoxy)phenyl]piperidine
1-allyl-4-[2-fluoro-3-(trifluoromethoxy)phenyl]piperidine
4-[2-chloro-3-(trifluoromethoxy)phenyl]-1-propylpiperidine
4-[2-chloro-3-(trifluoromethoxy)phenyl]-1-ethylpiperidine
1-allyl-4-[2-chloro-3-(trifluoromethoxy)phenyl]piperidine
3-(1-ethylpiperidin-4-yl)-2-methylbenzonitrile
3-(1-ethylpiperidin-4-yl)-2-fluorobenzonitrile
2-chloro-3-(1-ethylpiperidin-4-yl)benzonitrile
4-[2-fluoro-3-(trifluoromethyl)phenyl]-1-methylpiperidine
2-chloro-3-(1-methylpiperidin-4-yl)benzonitrile
4-[2-chloro-3-(trifluoromethyl) phenyl]-1-methylpiperidine
2-fluoro-3-(1-methylpiperidin-4-yl)benzonitrile The most preferred structures are:
4-(2,3-difluorophenyl)-1-propylpiperidine
4-(2,3-difluorophenyl)-1-ethylpiperidine
1-allyl-4-(2,3-difluorophenyl)piperidine
4-(2-chloro-3-fluorophenyl)-1-propylpiperidine
4-(2-chloro-3-fluorophenyl)-1-ethylpiperidine
1-allyl-4-(2-chloro-3-fluorophenyl)piperidine
4-[2-chloro-3-(trifluoromethyl)phenyl]-1-ethylpiperidine
4-(3-chloro-2-fluorophenyl)-1-propylpiperidine
4-(3-chloro-2-fluorophenyl)-1-ethylpiperidine
1-allyl-4-(3-chloro-2-fluorophenyl)piperidine
4-(2,3-dichlorophenyl)-1-propylpiperidine
4-(2,3-dichlorophenyl)-1-ethylpiperidine
1-allyl-4-(2,3-dichlorophenyl)piperidine
4-[3-(difluoromethoxy)-2-fluorophenyl]-1-propylpiperidine
4-[3-(difluoromethoxy)-2-fluorophenyl]-1-ethylpiperidine
1-allyl-4-[3-(difluoromethoxy)-2-fluorophenyl]piperidine
4-[2-chloro-3-(difluoromethoxy)phenyl]-1-propylpiperidine
4-[2-chloro-3-(difluoromethoxy)phenyl]-1-ethylpiperidine
1-allyl-4-[2-chloro-3-(difluoromethoxy)phenyl]piperidine
4-[2-fluoro-3-(trifluoromethoxy)phenyl]-1-propylpiperidine 1-ethyl-4-[2-fluoro-3-(trifluoromethoxy)phenyl]piperidine
1-allyl-4-[2-fluoro-3-(trifluoromethoxy)phenyl]piperidine
4-[2-chloro-3-(trifluoromethoxy)phenyl]-1-propylpiperidine
4-[2-chloro-3-(trifluoromethoxy)phenyl]-1-ethylpiperidine
1-allyl-4-[2-chloro-3-(trifluoromethoxy)phenyl]piperidine
3-(1-ethylpiperidin-4-yl)-2-fluorobenzonitrile
2-chloro-3-(1-ethylpiperidin-4-yl)benzonitrile
4-[2-fluoro-3-(trifluoromethyl)phenyl]-1-methylpiperidine
2-chloro-3-(1-methylpiperidin-4-yl)benzonitrile
4-[2-chloro-3-(trifluoromethyl)phenyl]-1-methylpiperidine
2-fluoro-3-(1-methylpiperidin-4-yl)benzonitrile The present invention also relates to intermediate compounds which are used in the synthesis of compounds of Formula 1. One such intermediate compound has the structure:

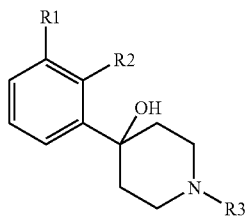

wherein $R_1$, $R_2$, $R_3$, are as defined above.

In this substructure, $R_1$ is preferably selected from the group consisting of —CN, —OCF$_3$, —OCHF$_2$, —SCF$_3$, —SCHF$_2$, —CF$_3$, F, Cl, —CH$_3$ and —OCH$_3$. More preferably, $R_1$ is selected from the group consisting of F, Cl and CF$_3$. Furthermore, $R_2$ is preferably selected from the group consisting of F and Cl. Intermediate compounds of interest are those in which $R_3$ is selected from the group consisting of n-propyl and ethyl. Intermediate compounds of most interest are those in which $R_2$ is F and $R_3$ is selected from the group consisting of n-propyl and ethyl.

Another intermediate in the synthesis of compounds with Formula 1 has the formula

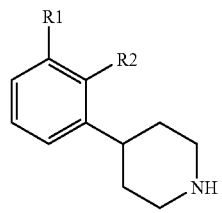

in which $R_1$ and $R_2$, are as defined above.

Such intermediate compounds of interest are those in which $R_1$ is selected from the group consisting of —CN, —OCF$_3$, —OCHF$_2$, —SCF$_3$, —SCHF$_2$, —CF$_3$, F, Cl, —CH$_3$ and —OCH$_3$. Further such intermediate compounds of interest are those in which $R_1$ is selected from the group consisting of CF$_3$, F, and Cl. Additionally, $R_2$ may be selected from the group consisting of F and Cl.

The invention also relates to the use of a compound of Formula 1 for the manufacture of a pharmaceutical composition for treatment of a disorder of the central nervous system. The present invention relates to a method for treating disorders of the central nervous system, by administrating a therapeutically active amount of a compound according to FIG. 1 to a mammal, including a human being, suffering from such a disorder. The present invention also relates to a method for treating any disorder named herein, by administrating a therapeutically active amount of a compound according to FIG. 1 to a mammal, including a human being, suffering from such a disorder.

The compounds according to the present invention possess dopamine-modulating properties and both they and their pharmaceutical compositions are useful in treating numerous central nervous system disorders, including both psychiatric and neurological disorders. Particularly, the compounds and their pharmaceutical compositions may be used in the treatment of CNS disorders were the dopaminergic system is dysfunctional due to direct or indirect causes.

The compounds and compositions according to the invention can be used to improve all forms of psychosis, including schizophrenia and schizophreniform and bipolar disorders as well as drug induced psychotic disorders. Iatrogenic and non-iatrogenic psychoses and hallucinoses may also be treated.

Mood and anxiety disorders, depression and obsessive-compulsive disease may also be treated with the compounds and compositions according to the invention.

Compounds with modulating effects on dopaminergic systems may also be used to improve motor and cognitive functions and in the treatment of emotional disturbances related to ageing, neurodegenerative (e.g. dementia and age-related cognitive impairment) and developmental disorders (such as Autism spectrum disorders, ADHD, Cerebral Palsy, Gilles de la Tourette's syndrome) as well as after brain injury. Such brain injury may be induced by traumatic, inflammatory, infectious, neoplastic, vascular, hypoxic or metabolic causes or by toxic reactions to exogenous chemicals, wherein the exogenous chemicals are selected from the group consisting of substances of abuse, pharmaceutical compounds, and environmental toxins The compounds and pharmaceutical compositions according to the invention may also be used in behavioural disorders usually first diagnosed in infancy, childhood, or adolescence as well as in impulse control disorders.

They can also be used for treating substance abuse disorders as well as disorders characterized by misuse of food. They are further useful for treatment of a condition selected from the group consisting of sleep disorders, sexual disorders, eating disorders, obesitas, and headaches and other pains in conditions characterized by increased muscular tone.

Neurological indications include the use of the compounds and their pharmaceutical compositions to improve mental and motor function in Parkinson's disease, and in related parkinsonian syndromes, dyskinesias (including L-DOPA induced dyskinesias) and dystonias. They may also be used to ameliorate tics and tremor of different origins. Moreover, they may be used to relieve pain in conditions characterized by increased muscle tone.

They can also be used in the treatment of Huntington's disease and other movement disorders as well as movement disorders induced by drugs. Restless legs and related disorders as well as narcolepsy may also be treated with compounds included according to the invention.

The compounds and their pharmaceutical compositions according to the present invention can be used for the treatment of Alzheimer's disease or related dementia disorders.

The compounds according to the present invention have been shown to display dopaminergic stabilizer profile with improved potency. They have effects on biochemical indices in the brain with the characteristic features of dopamine antagonists, e.g. producing increases in concentrations of dopamine metabolites.

The compounds of this invention show no, or only limited effects on spontaneous locomotion over a wide dose range (Table 2).

TABLE 2

Effects of compounds from the present invention on Locomotor activity in drug-naive rats. The animals were placed in the motility meters immediately after drug administration and locomotor activity was recorded for 60 minutes (counts/60 min ± SEM).

| | Control group | 11 µmol/kg | 33 µmol/kg | 100 µmol/kg |
|---|---|---|---|---|
| 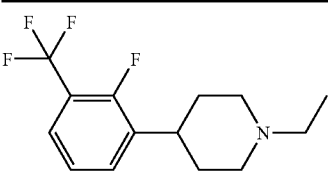 Example 3 | 12311 ± 1111 | 10587 ± 1027 | 6439 ± 418 | 4866 ± 941 |
| 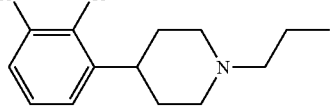 Example 6 | 10036 ± 1886 | 7739 ± 1903 | 7053 ± 659 | 4272 ± 1831 |
| 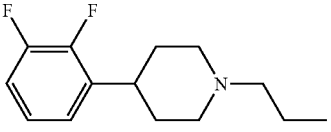 Example 5 | 12549 ± 368 | 8894 ± 1039 | 9958 ± 1835 | 8154 ± 1388 |

On the other hand, the preferred substances reduce the increase in activity induced by direct or indirect dopaminergic agonists, i.e. d-amphetamine and congeners (Table 3) and has been found to be more potent than the comparative examples.

TABLE 3

Effects of compounds in the present invention on reduction of amphetamine-induced hyper-locomotion. Comparative examples from prior art is also included. For methods and statistical calculations see the enclosed tests.

| Example | $ED_{50}$ µmol/kg | Comparative Examples | $ED_{50}$ µmol/kg |
|---|---|---|---|
| 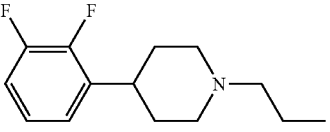 Example 5 | 17.1 (6.1-34) | 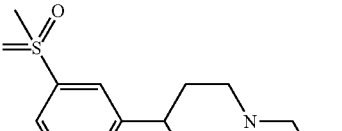 Example 6 of WO01/46145 | 52.0 (35-76) |
| 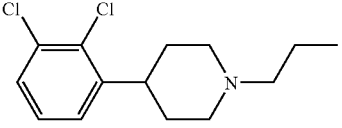 Example 6 | 11 (7.2-16) | 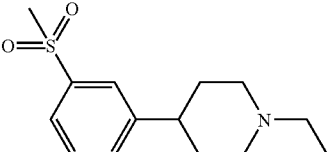 Example 12 of WO01/46145 | 86 (34-137) |

TABLE 3-continued

Effects of compounds in the present invention on reduction of amphetamine-induced hyper-locomotion. Comparative examples from prior art is also included. For methods and statistical calculations see the enclosed tests.

| Example | ED$_{50}$ µmol/kg | Comparative Examples | ED$_{50}$ µmol/kg |
|---|---|---|---|
| 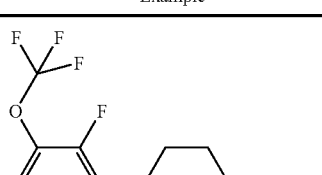<br>Example 2 | 9.0<br>(1.1-19) | 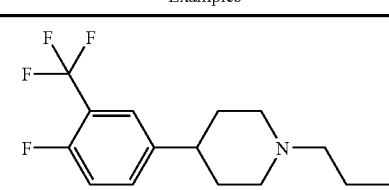<br>Example 43<br>of WO01/46146 | 30<br>(21-44) |
|  |  | 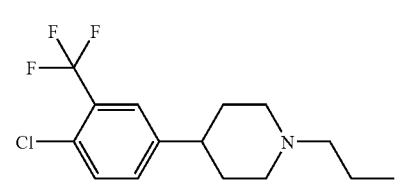<br>Example 9<br>of WO01/46146 | 34<br>(12-54) |
|  |  | 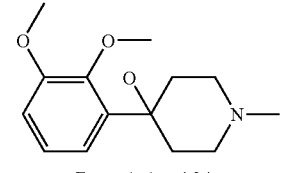<br>Example 1 and 2 in<br>U.S. Pat. No. 4,415,736 | inactive |

Thus, the compounds of this invention show a dopaminergic stabilizer profile (seen in Table 1-3) with improved potency (seen in Table 1 and 3). Given the involvement of dopamine in a large variety of CNS functions and the clinical shortcomings of presently available pharmaceuticals acting on dopamine systems, the novel class of dopaminergic modulators presented in this invention may prove superior to presently known dopaminergic compounds in the treatment of several disorders related to dysfunctions of the CNS, in terms of efficacy as well as side effects.

Compounds of the present invention have been estimated to display an oral bioavailability in rat of 15% or more.

These compounds are thus suitable for the preparation of orally-administered pharmaceuticals. There is no guidance in the prior art how to obtain compounds with the dopamine stabilizer profile (Table 1 to Table 3) with improved potency on dopamine systems in the brain.

Pharmacology

Evidence is available that dopaminergic neurotransmission in the CNS is disturbed in psychiatric and neurological diseases. In many instances, for example in schizophrenia, Parkinson's disease, Huntington disease, bipolar disorder and in dementia pharmacotherapies based on antagonism or agonism at dopamine receptors are useful, but not optimal. In recent years many efforts have been made in finding novel and selective compounds for dopamine receptor subtypes (D1, D2, D3, D4, D5) with the aim to improve efficacy and reduce side effects.

The present invention offers another principle for novel therapeutics based on interactions with the dopamine system. The invention provides compounds having, as their major feature, stabilizing effects on the dopaminergic system in the brain. They also have the property to increase serotonin levels in various brain regions, preferably the prefrontal cortex.

Description of Animal Models Used in the Invention

The compounds according to the invention have effects on brain neurochemistry similar to antagonists at dopamine D$_2$ receptors (i.e. dose-dependent increases of the dopamine metabolite DOPAC, in cortical, striatal and limbic brain regions). The compounds according to the invention show no, or only limited inhibitory, effects on spontaneous locomotion. Under certain conditions they can induce a behavioural activation. The behavioural activation is limited, not reaching the profound increases in activity induced by direct or indirect dopamine receptor agonists. However, the preferred substances reduce the increase in activity induced by the indirect dopaminergic agonist d-amphetamine. The increase in activity after treatment with d-amphetamine is a standard model of hyperdopaminergia (Table 3). In this model, dopaminergic neurotransmission is increased by systemic administration of d-amphetamine at a dose that is sufficiently high to produce a large increase in locomotor activity. The ability of a compound to antagonize this hyperactivity reflects anti-dopaminergic properties, which are part of the dopaminergic stabiliser profile. Furthermore, antagonism of d-amphetamine induced hyperactivity is widely used as a standard assay of antipsychotic activity (see *Psychopharmacology* 4th *Generation of* progress Chapter 68, p 793-795). The compounds of the present invention were also found to be more potent compared to known dopamine antagonists.

Another animal model of antipsychotic activity is based on administration of the glutamate antagonist MK-801. Glutamate antagonists (i.e. NMDA antagonists), can induce psychoses in man (see *Psychopharmacology, 4th Generation of progress* Chapter 101, p. 1205 and 1207) and induce behavioural aberrations in animals. Thus, the ability of a drug to affect schizophrenia and psychotic states can be measured using behavioural models based on experimentally-induced hypoglutamatergic states. In this study the NMDA antagonist MK-801 (0.7 mg/kg i.p.) was used to create a hypoglutamatergic state where the rats display abnormal, hyperactive behaviour. Compounds in the present invention dose-dependently reverse the behavioural aberration induced by MK-801 (see Table 4).

It is known that the dopaminergic systems of the brain interact strongly with other transmitter systems (see *Psychopharmacology, 4th Generation of progress*, Chapter 101, pages 1208-1209). Such interactions can explain the powerful effects of dopaminergic stabilizers on the behavioural aberrations induced by the glutamate antagonist MK-801 although these aberrations are not primarily based on or caused by changes in dopaminergic transmission.

wuegi 2004). Serotonin-selective re-uptake inhibitors (SSRIs) are the most widely prescribed antidepressant drugs. The finding that drugs which preferentially increase serotonin activity by decreasing its re-uptake are effective in the treatment of depression is the most compelling evidence for the importance of serotonin in regulation of mood. (Fuller 1995; Dursun, Blackburn et al. 2001).

The microdialysis technique (Ungerstedt, Herrera-Marschitz et al. 1982) is a well established technique for measuring extracellular levels of neurotransmitters (Ungerstedt 1991). The microdialysis technique was used to measure the effect of drugs upon the monoamine transmitters. The appended graphs (FIGS. 1-4) show the effects of one established antidepressant (citalopram) upon 5-HT in the cortex, as well as for three compounds claimed in the present invention (Examples 3, 5, and 6). For both the established antidepressants and the novel compounds of the present invention, a 5-HT increase in the cortex is given, therefore we argue that Example 3, Example 5 and Example 6 in the present invention are antidepressants.

List of Abbreviations:

NA: norepinephrine, NM: normetanephrine; DA: dopamine, 3-MT: 3-methoxytyramine; 5-HT: serotonin (5-hydroxytryptamine).

TABLE 4

Effects of compounds from the present invention on Locomotor activity in MK-801 pretreated rats (0.7 mg/kg i.p. 90 minutes before test compound). The animals were placed in the motility meters immediately after test compound administration and locomotor activity was recorded between 30 and 60 minutes after administration (counts/30 min ± SEM)

|  | Control group | MK-801 0.7 mg/kg i.p. | MK + example 33 µmol/kg |
|---|---|---|---|
| 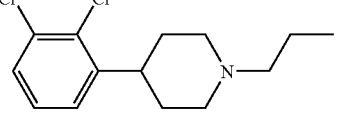 Example 6 | 89 ± 38 | 30462 ± 6937 | 12943 ± 3226 (P = 0.06) |
| 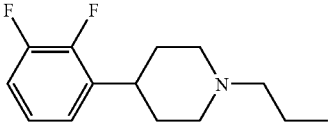 Example 5 | 763 ± 672 | 55810 ± 16124 | 19826 ± 6949 (P = 0.09) |

Effects on Serotonin Levels in Cortical Regions

5-Hydroxytryptamine (5-HT, serotonin) was detected in the brain in the 1950's. Over the past decades, research has implicated the brain monoamines in the etiology of depression. While early evidence favored dysfunction in the catecholamine systems, more recent evidence has implicated serotonergic mechanisms to the point where the "serotonin hypothesis" is the most widely accepted of any account of the neural basis of depression (Dursun, Blackburn et al. 2001).

Evidence suggests that the activity of the monoamines, including serotonin, is decreased in depression. All effective pharmacotherapeutic agents, as well as other forms of depression treatments, modify monoamine transmitter function (Owens 2004). There are now several lines of evidence suggesting that antidepressant therapy relieves depression through an increased activity of the serotonergic system (Carlsson, Fuxe et al. 1968; Lapin and Oxenkrug 1969; Elh- FIG. 1. Citalopram 5 mg/kg s.c. cortex Citalopram is injected (s.c) at time-point 0. The values depicted in the graph represent percent of control in relation to baseline values. The microdialysis was performed in awake and freely moving rats. Error-bars=SEM FIG. 2. Example 3, 50 µmol/kg s.c. pf. cortex amines n: 1-2

Example 3 is injected (s.c.) at time-point 0. The values depicted in the graph represent percent of control in relation to baseline values. The microdialysis was performed in awake and freely moving rats. Error-bars=SEM FIG. 3. Example 5, 50 µmol/kg s.c. pf. cortex amines n: 1-2

Example 5 is injected (s.c.) at time-point 0. The values depicted in the graph represent percent of control in relation to baseline values. The microdialysis was performed in awake and freely moving rats. Error-bars=SEM FIG. 4. Example 6, 50 µmol/kg s.c. of. cortex amines n: 1-2

Example 6 is injected (s.c.) at time-point 0. The values depicted in the graph represent percent of control in relation to baseline values. The microdialysis was performed in awake and freely moving rats. Error-bars=SEM Some antidepressants have a predominant effect upon the extracellullar levels of norepinephrine and dopamine versus 5-HT in the cortex, as measured by microdialysis.

The common trait for all clinically effective classes of antidepressants is an elevation of the levels of dopamine and norepinephrine in the cortex (Tanda, Carboni et al. 1994; Millan, Lejeune et al. 2000). The clinically effective antdepressant mirtazapine (remeron) has been shown to increase predominantly extracellullar norepinephrine and dopamine in the cortex (See FIG. 5, Devoto, Flore et al. 2004). We argue that the compounds (Example 3, 5 and 6) claimed in the present invention function as antidepressants due to an elevation of 5-HT levels in the cortex. As the compounds claimed in the present invention also elevate the levels of dopamine and norepinephrine in the cortex this further strengthens our claim that they function as antidepressants (see FIG. 2-4, Example 3, 5 and 6 in the present invention).

Figure 5:
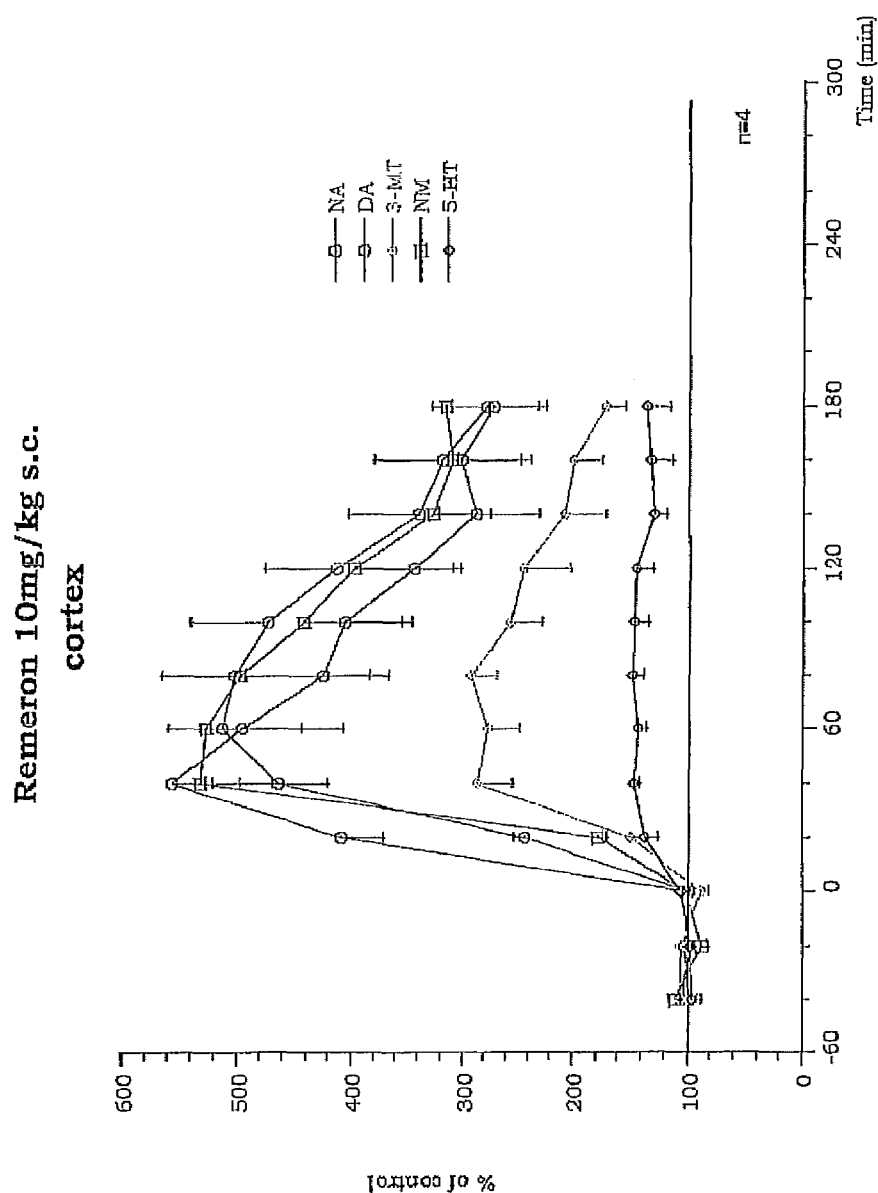

FIG. 5. Remeron 10 mg/kg s.c. cortex

Remeron is injected (s.c.) at time-point 0. The values depicted in the graph represent percent of control in relation to baseline values. The microdialysis was performed in awake and freely moving rats. Error-bars=SEM

REFERENCES

Carlsson, A., K. Fuxe and U. Ungerstedt (1968). "The effect of imipramine on central 5-hydroxytryptamine neurons." J Pharm Pharmacol 20(2): 150-1.

Dursun, S. M., J. R. Blackburn and S. P. Kutcher (2001). "An exploratory approach to the serotonergic hypothesis of depression: bridging the synaptic gap." Med Hypotheses 56(2): 235-43.

Elhwuegi, A. S. (2004). "Central monoamines and their role in major depression." Prog Neuropsychopharmacol Biol Psychiatry 28(3): 435-51.

Fuller, R. W. (1995). "Serotonin uptake inhibitors: uses in clinical therapy and in laboratory research." Prog Drug Res 45: 167-204.

Lapin, I. P. and G. F. Oxenkrug (1969). "Intensification of the central serotoninergic processes as a possible determinant of the thymoleptic effect." Lancet 1(7586): 132-6.

Owens, M. J. (2004). "Selectivity of antidepressants: from the monoamine hypothesis of depression to the SSRI revolution and beyond." J Clin Psychiatry 65 Suppl 4: 5-10.

Ungerstedt, U. (1991). "Microdialysis-principles and applications for studies in animals and man." J. Int. Med. 230: 365-373.

Ungerstedt, U., M. Herrera-Marschitz, U. Jungnelius, L. Stahle, U. Tossman and T. Zetterström (1982). Dopamine Synaptic Mechanisms Reflected in Studies Combining Behavioural Recordings and Brain Dialysis. Advances in Dopamine Research. M. Kohksa. Oxford, Perganon Press. 37: 219-231.

Devoto, P., G. Flore, L. Pira, G. Longu and G. L. Gessa (2004). "Mirtazapine-induced corelease of dopamine and noradrenaline from noradrenergic neurons in the medial prefrontal and occipital cortex." Eur J Pharmacol 487(1-3): 105-11.

Millan, M. J., F. Lejeune and A. Gobert (2000). "Reciprocal autoreceptor and heteroreceptor control of serotonergic, dopaminergic and noradrenergic transmission in the frontal cortex: relevance to the actions of antidepressant agents." J Psychopharmacol 14(2): 114-38.

Tanda, G., E. Carboni, R. Frau and G. Di Chiara (1994). "Increase of extracellular dopamine in the prefrontal cortex: a trait of drugs with antidepressant potential?" Psychopharmacology (Berl) 115(1-2): 285-8.

Therapeutic Use of Dopaminergic Stabilizers

The claimed invention provides compounds having, as their major feature, stabilizing effects on the dopaminergic system in the brain, but also effects on the serotonin system. These compounds are useful for treating CNS disorders in which the symptoms can be affected by dopaminergic functions. In support of this assertion, please see the following references:

In support of schizophrenia and psychosis, Applicants refer to *Psychopharmacology 4th Generation of progress* Chapter 26, p. 295-301;

Parkinson's disease (*Psychopharmacology 4th Generation of progress* Chapter 26, p 295, Chapter 1479-1482);

Anxiety disorders (*Psychopharmacology 4th Generation of progress* Chapter 21, p. 227 and 237, Chapter 111, p. 1317-1318 and 1320);

Mood disorders (*Psychopharmacology 4th Generation of progress* Chapter 80, p. 921-928; and Substance abuse (*Psychopharmacology 4th Generation of progress* Chapter 25, p. 283 and 292, Chapter 66, p. 759-760, Chapter 147, p. 1725 (see also Nisell et al., "Systemic Nicotine-Induced Dopamine Release in the Rat Nucleus Accumbens is Regulated by Nicotinic receptors in the Ventral Tegmental Area; *Synapse* (1994) 16: 36-44). Chapter 149, p. 1745-1747 and 1751-1752). Drugs abused by humans preferentially increase synaptic dopamine concentrations in the mesolimbic system of freely moving rats Di Chiara et al *Proc Natl Acad Sci USA* 85, 5274, 1988. Drug addiction as a disorder of associative learning. Role of nucleus accumbens shell/extended amygdala dopamine *Ann N.Y. Acad Sci* 877, 461, 1999.

As shown by these references, the claimed conditions are recognized in the art as diseases which concern dopaminergic and serotonergic neurotransmission Furthermore, pharmacological interaction with dopaminergic neurotransmission is widely believed to be useful in the treatment of several CNS disorders, which are not generally believed to be directly caused by disruptions in dopaminergic neurotransmission. For example, the symptoms of Huntington's disease and other movement disorders can be treated with dopaminergic agents due to the involvement of dopamine in motor functions—(see *Psychopharmacology 4th Generation of progress*, Chapter 26, p. 295-301). Likewise, it is known that cognitive disorders (see *Psychopharmacology 4th Generation of progress* Chapters 25, p. 292, Chapter 120, p. 1417 and 1420, Chapter 123, p. 1447 and 1452 and 1455-1457) autism (see *Psychopharmacology 4th Generation of progress* Chapter 142, p. 1653 and 1661), attention-deficit hyperactivity disorder (see *Psychopharmacology 4th Generation of progress* Chapter 141, p. 1643 and 1649-1650), sexual disorders (see *Psychopharmacology 4th Generation of progress* Chapters 65, p. 743-746 and Chapter 22, p. 245 and 254) and eating disorders (see *Psychopharmacology 4th Generation of progress* Chapters 137, p. 1600, Chapter 138, p. 1609-1610 and 1612) may be treated with agents which interact with dopaminergic transmission. Thus, the above references support the argument that the compounds of the invention would be useful in the treatment of such diseases.

Methods of Preparation

The compounds of the invention may be prepared as outlined below in Schemes 1-3. However, the invention is not limited to these methods. The compounds may also be prepared as described for structurally-related compounds in the prior art. The reactions can be carried out according to standard procedures[1,2] or as described in the working examples. The starting materials for the processes described in the present application are known or may readily be prepared by conventional methods from commercially available chemicals.

Persons skilled in the art will appreciate that, in order to obtain compounds of the invention in an alternative—and in some occasions, more convenient manner—the individual process steps mentioned hereinbefore may be performed in a different order, and/or the individual reactions may be performed at different stage in the overall route (i.e. chemical transformations may be performed upon different intermediates to those associated hereinbefore with a particular reaction).

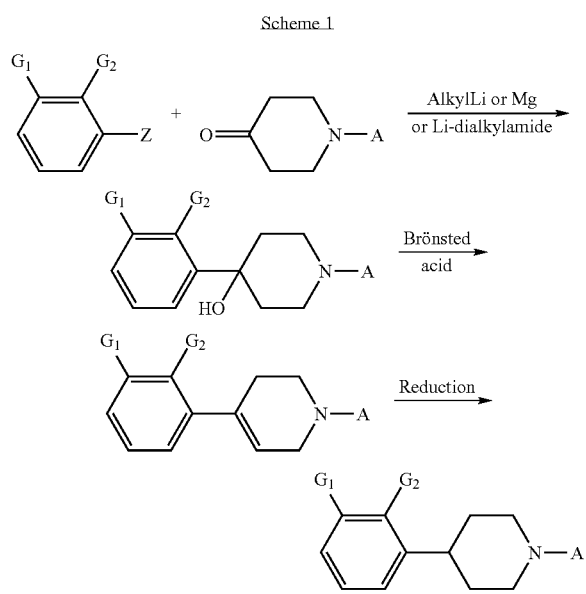

Scheme 1

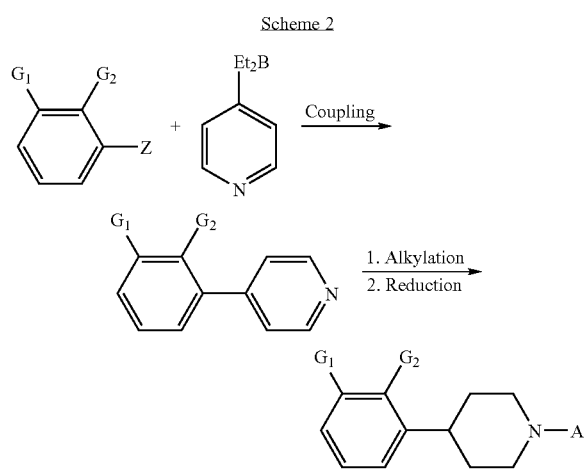

Scheme 2

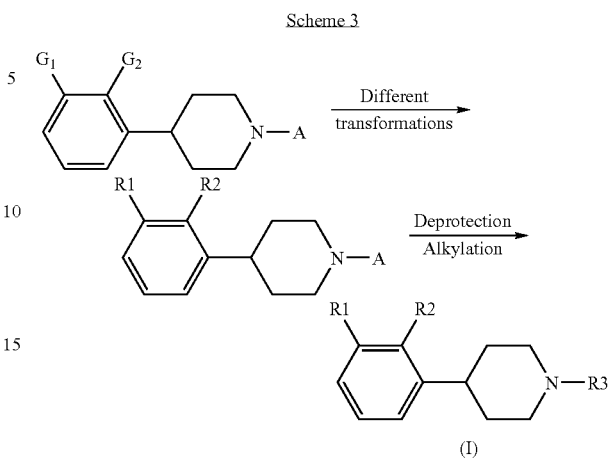

Scheme 3

The substituents in Scheme 1-3, are as follows: Z is a leaving group, G1 is R1 or a group that can be transformed into R1, G2 is R2 or a group that can be transformed into R2, A is alkyl, hydrogen or a protecting group. X, R1, R2 and R3 are as defined above.

REFERENCES

1. *Comprehensive Organic Transformations: A Guide to Functional Group Preparations* Richard C. Larock, 22 Oct., 1999 Wiley-VCH, ISBN: 0471190314
2. *March's Advanced Organic Chemistry: Reactions, Mechanisms, and Structure, 5th Edition.* Michael B. Smith, Jerry March, Jan. 15, 2001 Wiiey-Interscience, ISBN: 0471585890

The term "patient" used herein refers to an individual in need of the treatment according to the invention.

The term "treatment" used herein relates to both treatment in order to cure or alleviate a disease or a condition and to treatment in order to prevent the development of a disease or a condition. The treatment may either be performed in an acute or in a chronic way.

Any chemical formula or name given herein is meant to include all stereo and optical isomers and racemates and mixtures thereof in any ratio. The various isomers can be obtained by standard methods well known to persons skilled in the art, e.g. via chromatography or fractional crystallisation. For example, cis/trans mixtures can be separated into the individual stereoisomers by stereoselective synthesis. Enantiomers or diastereomers may be isolated by separation of their mixtures, for instance by fractional crystallisation, resolution or HPLC. Alternatively separation can be afforded by derivatisation with a chiral reagent. Stereoisomers may be made by stereoselective synthesis from stereochemically pure starting materials under conditions which will not cause loss of stereochemical integrity. All stereoisomers are included within the scope of the invention.

The compounds of the present invention may be isolated in any level of purity by standard methods and purification can be achieved by conventional means known to those skilled in the art, such as distillation, recrystallization and chromatography.

The present invention relates to pharmaceutical compositions comprising the compounds of the present invention, and their use in treating CNS disorders. Both organic and inorganic acids can be employed to form non-toxic pharmaceutically acceptable acid addition salts of the compounds according to the invention. Suitable acid addition salts of the compounds of the present invention include those formed with pharmaceutically acceptable salts such as toluensulfonate, methanesulfonate, fumarate, hydrochloride, hydrobromide, hydroiodide, nitrate, acetate, lactate, citrate, acid citrate, tartrate, bitartrate, aliphatic, alicyclic, aromatic or heterocyclic carboxylate, succinate, maleate, fumarate, gluconate, glycolate, saccharate, ascorbate, acetate, propionate, benzoate, pyruvate, pamoate [i.e., 1,1'-methylene-bis-(2-hydroxy-3-naphthoate)], phosphate, acid phosphate, sulphate or bisulfate salts. These salts are readily prepared by methods known in the art. It is also to be understood that compounds of the present invention can exist in solvated as well as unsolvated forms such as, e.g, hydrated forms.

The pharmaceutical composition comprising a compound according to the invention may also comprise substances used to facilitate the production of the pharmaceutical preparation or the administration of the preparations. Such substances are well known to people skilled in the art and may for instance be pharmaceutically acceptable adjuvants, carriers and preservatives.

In clinical practice, the compounds according to the present invention will normally be administered orally, rectally, nasally or by injection, in the form of pharmaceutical preparations comprising the active ingredient either as a free base or as a pharmaceutically acceptable non-toxic, acid addition salt, such as the hydrochloride, lactate, acetate or sulfamate salt, in association with a pharmaceutically acceptable carrier. The carrier may be a solid, semisolid or liquid preparation. Usually the active substance will constitute between 0.1 and 99% by weight of the preparation, more specifically between 0.5 and 20% by a weight for preparations intended for injection and between 0.2 and 50% by weight for preparations suitable for oral administration.

To produce pharmaceutical preparations containing the compound according to the invention in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinyl-pyrrolidone, and a lubricant such as magnesium stearate, calcium stearate, polyethylene glycol, waxes, paraffin, and the like, and then compressed into tablets. If coated tablets are required, the cores (prepared as described above) may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compound.

For the preparation of soft gelatine capsules, the active substance may be admixed with e.g. a vegetable oil or polyethylene glycol. Hard gelatine capsules may contain granules of the active substance using either the mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Examples of tablet and capsule formulations suitable for oral administration are given below:

| Tablet I | mg/tablet |
|---|---|
| Compound | 100 |
| Lactose Ph. Eur | 182.75 |
| Croscarmellose sodium | 12.0 |
| Maize starch paste (5% w/v paste) | 2.25 |
| Magnesium stearate | 3.0 |

| Tablet II | mg/tablet |
|---|---|
| Compound | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| Tablet III | mg/tablet |
|---|---|
| Compound | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| Capsule | mg/capsule |
|---|---|
| Compound | 10 |
| Lactose Ph. Eur | 488.5 |
| Magnesium | 1.5 |

Dosage units for rectal application can be solutions or suspensions or can be prepared in the form of suppositories comprising the active substance in a mixture with a neutral fatty base, or gelatine rectal capsules comprising the active substance in admixture with vegetable oil or paraffin oil. Liquid preparations for oral application may be in the form of syrups or suspensions, for example solutions containing from about 0.2% to about 20% by weight of the active substance herein described, the balance being sugar and mixture of ethanol, water, glycerol and propylene glycol. Optionally such liquid preparations may contain coloring agents, flavoring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from 0.5% to about 10% by weight. These solutions may also containing stabilizing agents and/or buffering agents and may conveniently be provided in various dosage unit ampoules. The use and administration to a patient to be treated would be readily apparent to an ordinary skill in the art.

For intranasal administration or administration by inhalation, the compounds of the present invention may be delivered in the form of a solution, dry powder or suspension. Administration may take place via a pump spray container that is squeezed or pumped by the patient or through an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. The compounds of the invention may also be administered via a dry powder inhaler, either as a finely divided powder in combination with a carrier substance (e.g. a saccharide) or as microspheres. The inhaler, pump spray or aerosol spray may be single or multi dose. The dosage may be controlled through a valve that delivers a measured amount of active compound.

The compounds of the invention may also be administered in a controlled release formulation. The compounds are released at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. The compounds may also be formulated in controlled release formulations in which release of the active compound is targeted. For example, release of the compound may be limited to a specific region of the digestive system through the pH sensitivity of the formulation. Such formulations are well known to persons skilled in the art.

Depending upon the disorder and patient to be treated and the route of administration, the compositions may be administered at varying doses. The dosing will also depend upon the relation of potency to absorbability and the frequency and route of administration. Such doses may be administered once, twice or three or more times daily. The compounds of this invention can be administered to subjects in doses ranging from 0.01 mg to 500 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for the treatment of diseases. Alternatively, the dosage level is such that a serum concentration of between 0.1 nM to 10 µM of the compound is obtained.

The invention is further illustrated in the examples below, which in no way are intended to limit the scope of the invention.

EXAMPLE 1

1-ethyl-4-[2-fluoro-3-(trifluoromethoxy)phenyl]piperidine

Preparation according to Example 8: 4-[2-fluoro-3-(trifluoromethoxy)phenyl]piperidine (0.70 g, 2.66 mmol), acetonitrile (4 ml), potassium carbonate (0.92 g, 6.65 mmol), 1-iodoethane (0.275 ml, 2.93 mmol). Yield: 0.7 g. MS m/z (rel. intensity, 70 eV) 291 (M+, 14), 290 (10), 277 (15), 276 (bp), 193 (8).

EXAMPLE 2

4-[2-fluoro-3-(trifluoromethoxy)phenyl]-1-propylpiperidine

A mixture of 4-[2-fluoro-3-(trifluoromethoxy)phenyl]-1-propyl-1,2,3,6-tetrahydro-pyridine (0.55 g, 1.8 mmol), palladium on carbon (0.09 g), hydrochloric acid (0.5 ml, conc), in methanol (30 ml) was hydrogenated at 50 psi for 15 h under hydrogen. The reaction mixture was filtered through a pad of celite and the filtrate was concentrated and evaporated to dryness to give 0.55 g of crude product. Purification by flash column chromatography (Isooctane/ethylacetate, 1:1) gave the title compound 0.22 g (40%). The amine was converted to the hydrochloric acid salt and recrystallized from ethanol/diethyl ether: M.p. 221-222° C. MS m/z (relative intensity, 70 eV) 305 (M+, 3), 277 (14), 276 (bp), 233 (6) 193 (8).

EXAMPLE 3

4-[2-fluoro-3-(trifluoromethyl)phenyl]-1-ethylpiperidine

Preparation according to Example 2: 1-ethyl-4-[2-fluoro-3-(trifluoromethyl)phenyl]-1,2,3,6-tetrahydropyridine (3.1 g, 11.3 mmol), palladium on carbon (0.3 g), hydrochloric acid (1.5 ml, conc), methanol (30 ml). Yield: 2.3 g (74%). The amine was converted to the hydrochloric acid salt and recrystallized from ethanol/diethyl ether: M.p. 235-237° C. MS m/z (relative intensity, 70 eV) 275 (M+, 12), 261 (16), 260 (bp), 177 (10) 84 (13).

EXAMPLE 4

3-(1-ethylpiperidin-4-yl)-2-fluorobenzonitrile

To a solution of 3-(1-ethylpiperidin-4-yl)-2-fluorobenzamide (0.46 g, 1.83 mmol) in dry N,N-dimethylformamide (4 ml) was added freshly distilled phosphoryl trichloride (0.42 ml, 4.57 mmol) and the reaction mixture was stirred for 1 h. The solution was poured on to ice and was made basic by addition of aqueous sodium carbonate (10%, 50 ml). Ethyl acetate (50 ml) was added and the phases were separated. The aqueous phase was extracted with ethyl acetate (2×50 ml) and the combined organic phases was dried (MgSO4) and evaporated under reduced pressure to give an oil. Purification by flash column chromatography (ethyl acetate/methanol, 1:1) gave the title compound: 0.32 g (75%). The amine was converted to the oxalic acid salt and recrystallized from ethanol/diethyl ether: M.p. 156-158° C. MS m/z (relative intensity, 70 eV) 232 (M+, 12), 218 (14), 217 (bp), 147 (10), 134 (13).

EXAMPLE 5

4-(2,3-difluorophenyl)-1-propylpiperidine

Preparation according to Example 2: 4-(2,3-difluorophenyl)-1-propyl-1,2,3,6-tetrahydropyridine (3.35 g, 14.1 mmol), methanol (30 ml), palladium on carbon (0.8 g) and hydrochloric acid (1.5 ml, conc). Yield: 1.29 g (38%). The amine was converted to the hydrochloric acid salt and recrystallized from ethanol/diethyl ether: M.p. 237-238° C. MS m/z (relative intensity, 70 eV) 239 (M+, 4), 211 (13), 210 (bp), 127 (20) 70 (38).

EXAMPLE 6

4-(2,3-dichlorophenyl)-1-propylpiperidine

A mixture of 4-(2,3-dichlorophenyl)-1-propyl-1,2,3,6-tetrahydropyridine (0.4 g, 1.48 mmol), platinum oxide (0.05 g) and hydrochloric acid (0.1 ml, conc) in methanol (30 ml) was hydrogenated at 50 psi for 1 h under hydrogen gas. The reaction mixture was filtered through a pad of celite and the filtrate was concentrated and evaporated to dryness to give 0.4 g of the title compound as the hydrochloric acid salt (87%).

Recrystallization from ethanol/diethyl ether: M.p. 265-267° C. MS m/z (relative intensity, 70 eV) 271 (M+, 4), 243 (66), 242 (bp), 164 (9) 115 (17).

EXAMPLE 7

4-(2,3-dichlorophenyl)-1-methylpiperidine

A mixture of 4-(2,3-dichlorophenyl)piperidine (20 mg, 0.064 mmol), 1,2-dichloroethane (1 ml), glacial acetic acid (4 mg, 0.064 mmol), paraformaldehyde (2 mg, 0.066 mmol) and sodium triacetoxyborohydride (20 mg, 0.092 mmol) was stirred 15 h at ambient temperature. MS m/z (rel. intensity, 70 eV) 244 (M+, 68), 243 (54), 242 (bp), 208 (61), 115 (29).

EXAMPLE 8

4-(2,3-dichlorophenyl)-1-ethylpiperidine

To a solution of 4-(2,3-dichlorophenyl)piperidine (10 mg) in acetonitrile (2 ml), was added potassium carbonate (10 mg) and 1-iodoethane (5 mg) and the mixture was heated to 140° C. in a sealed tube under microwave radiation for 400 s. MS m/z (rel. intensity, 70 eV) 258 (M+, 11), 257 (18), 256 (14), 244 (66), 242 (bp).

EXAMPLE 9

4-(2,3-difluorophenyl)-1-methylpiperidine

To a solution of 4-(2,3-difluorophenyl)piperidine (0.2 g, 1.01 mmol) in acetonitrile (10 ml), was added potassium carbonate (0.28 g, 2.0 mmol) and 1-iodomethane (0.06 ml, 1.0 mmol) and the mixture was stirred at ambient temperature for 1 h. MS m/z (rel. intensity, 70 eV) 211 (M+, 78), 210 (bp), 2140 (8), 127 (12), 97 (11).

EXAMPLE 10

4-(2,3-difluorophenyl)-1-ethylpiperidine

To a solution of 4-(2,3-difluorophenyl)piperidine (0.41 g, 2.08 mmol) in acetonitrile (4 ml), was added potassium carbonate (0.57 g, 4.16 mmol) and 1-iodoethane (0.163 ml, 2.12 mmol) and the mixture was heated to 120° C. in a sealed tube under microwave radiation for 1200 s. Water (50 ml) was added and the mixture was extracted with ethylacetate (3×40 ml). The combined organic phases was dried (MgSO$_4$), filtered and evaporated to dryness. The oily residue was purified by flash column chromatography (ethylacetate/methanol, 1:1) to give the title compound (0.31 g). MS m/z (reL. intensity, 70 eV) 225 (M+, 20), 224 (14), 211 (13), 210 (bp), 127 (8).

EXAMPLE 11

4-[2-fluoro-3-(trifluoromethyl)phenyl]-1-methylpiperidine

Preparation according to Example 2: 4-[2-fluoro-3-(trifluoromethyl)phenyl]-1-methyl-1,2,3,6-tetrahydropyridine (0.59 g, 2.28 mmol), methanol (30 ml), palladium on carbon (0.07 g) and hydrochloric acid (0.1 ml, conc). Yield: 0.43 g. The amine was converted to the hydrochloric acid salt and recrystallized from ethanol/diethyl ether: M.p. 260-261° C. MS m/z (relative intensity, 70 eV) 261 (M+, 69), 260 (bp), 242 (9), 97 (12) 70 (37).

EXAMPLE 13

4-[3-(difluoromethoxy)-2-fluorophenyl]-1-ethylpiperidine

To a solution of 3-(1-ethylpiperidin-4-yl)-2-fluorophenol (0.43 g, 1.9 mmol) ) in isopropanol (5 ml) and aqueous sodium hydroxide (30%, 5 ml) was added chlorodifluoromethane gas through a liner for 1 min. The mixture was heated to 65° C. and bubbling of chlorodifluoromethane was continued for an additional 30 min. Water (50 ml) was added and the mixture was extracted with ethylacetate (3×50 ml). The combined organic phases was dried (MgSO$_4$), filtered and evaporated to dryness. MS m/z (rel. intensity, 70 eV) 273 (M+, 14), 272 (13), 259 (12), 258 (bp), 84 (13).

Synthesis of intermediates used in the above Examples are described in the preparations below.

PREPARATION 1

4-[2-fluoro-3-(trifluoromethyl)phenyl]-1,2,3,6-tetrahydropyridine

Preparation according to preparation 4: tert-butyl 4-[2-fluoro-3-(trifluoromethyl)phenyl]-4-hydroxypiperidine-1-carboxylate (8.5 g, 23.4 mmol), polyphosphoric acid (30 ml). Yield: 4.2 g. MS m/z (rel. intensity, 70 eV) 245 (M+, bp), 244 (52), 177 (45), 147 (99), 82 (96).

PREPARATION 2

4-[2-fluoro-3-(trifluoromethyl)phenyl]piperidine

Preparation according to Example 2: 4-[2-fluoro-3-(trifluoromethyl)phenyl]-1,2,3,6-tetrahydropyridine (4.2 g, 17.1 mmol), methanol (20 ml), palladium on carbon (0.42 g) and hydrochloric acid (0.2 ml, conc). Yield: 1.8 g. MS m/z (relative intensity, 70 eV) 247 (M+, 22), 190 (8), 177 (5), 169 (7) 56 (bp).

PREPARATION 3

4-[2-fluoro-3-(trifluoromethoxy)phenyl]-1-propylpiperidin-4-ol

To a solution of 1-fluoro-2-(trifluoromethoxy)benzene (1.22 g, 6.77 mmol) in dry tetrahydrofurane (30 ml) at −78° C., under nitrogen, lithium diisopropylamide (2.5 M in hexane, 3.0 ml, 7.45 mmol) was added dropwise. The mixture was stirred for 1 h after which a solution of newly distilled 4-propyl-1-piperidone (0.96 g, 6.77 mmol) in dry tetrahydrofuran (20 ml) was added dropwise. The resulting mixture was stirred at −78° C. for 30 min and then brought to ambient temperature. Water (100 ml) was added and the mixture was extracted with ethylacetate (3×100 ml). The combined organic phases was dried (MgSO$_4$), filtered and evaporated to dryness. The oily residue was purified by flash column chromatography (ethylacetate/methanol, 1:1) to give the title compound (0.83 g). MS m/z (rel. intensity, 70 eV) 321 (M+, 5), 293 (14), 292 (bp), 274 (25), 207 (10).

PREPARATION 4

4-[2-fluoro-3-(trifluoromethoxy)phenyl]-1-propyl-1,2,3,6-tetrahydropyridine

A mixture of 4-[2-fluoro-3-(trifluoromethoxy)phenyl]-1-propyl-piperidin-4-ol (0.83 g, 2.6 mmol) and polyphosphoric acid (10 ml) was heated at 100° C. for 2 h. The mixture was poured on to ice and was basified with 5 M sodium hydroxide.

The mixture was extracted with ethylacetate (3×100 ml) and the combined organic phases was dried (MgSO$_4$), filtered and evaporated to dryness to give the title compound (0.62 g). MS m/z (rel. intensity, 70 eV) 303 (M+, 24), 275 (14), 274 (bp), 147 (7), 133 (6).

PREPARATION 5

4-[2-fluoro-3-(trifluoromethyl)phenyl]-1-ethylpiperidin-4-ol

To a solution of 3-Bromo-2-fluorobenzotrifluoride (5.0 g, 20.6 mmol) in dry tetrahydrofuran (50 ml), under nitrogen, was added dropwise at −78° C., n-butyllithium (2.5 M in hexane, 9.0 ml, 22.5 mmol). The mixture was stirred for 1 h after which a solution of newly distilled 4-ethyl-1-piperidone (2.6 g, 20.6 mmol) in dry tetrahydrofuran (30 ml) was added dropwise. The resulting mixture was stirred at −78° C. for 30 min and then brought to ambient temperature. Water (100 ml) was added and the mixture was extracted with ethylacetate (3×100 ml). The combined organic phases was dried (MgSO$_4$), filtered and evaporated to dryness. The oily residue was purified by flash column chromatography (ethylacetate/methanol, 1:1) to give the title compound. Yield: 4.0 g. MS m/z (rel. intensity, 70 eV) 291 (M+, 18), 277 (15), 276 (bp), 258 (37), 191 (27).

PREPARATION 6

4-[2-fluoro-3-(trifluoromethyl)phenyl]-1-ethyl-1,2,3,6-tetrahydropyridine

Preparation according to preparation 4: 4-[2-fluoro-3-(trifluoromethyl)phenyl]-1-ethylpiperidin-4-ol (3.3 g, 11.3 mmol), hydrochloric acid (10 ml, conc). Yield: 3.1 g. MS m/z (rel. intensity, 70 eV) 273 (M+, 65), 272 (32), 258 (bp), 147 (24), 110 (22).

PREPARATION 7

3-bromo-2-fluorobenzoic Acid

To a solution of 1-bromo-2-fluorobenzene (6.0 g, 34.3 mmol) in dry tetrahydrofuran (50 ml) under nitrogen, at −78° C. was added lithium diisopropylamide (2.5 M in hexane, 18.8 ml, 37.7 mmol). The mixture was stirred for 50 minutes and then poured onto crushed solid carbon dioxide. The reaction mixture was brought to ambient temperature and aqueous sodium carbonate (10%, 50 ml) was added. The aqueous phase was first washed with diethyl ether (2×100 ml), and then made acidic by addition of aqueous hydrochloric acid. The acidified aqueous phase was extracted with ethyl acetate (2×50 ml) and the combined organic phases was dried (MgSO4) and evaporated to dryness to give the title compound (4.24 g).

PREPARATION 8

3-bromo-2-fluorobenzamide

To a solution of 3-bromo-2-fluorobenzoic acid (3.77 g, 17.2 mmol) in dry tetrahydrofuran (200 ml) was added triethylamine (4.77 ml, 34.4 mmol) and thionyl chloride (1.69 ml, 21.5 mmol). The reaction mixture was stirred for 1 h and then quenched with ammonia in methanol (10 ml, saturated). After an additional hour of stirring the mixture was evaporated and the crude product was purified by flash column chromatography (ethyl acetate/isooctane 1:1) to give the title compound (1.76 g). MS m/z (rel. intensity, 70 eV) 219 (M+, 26), 217 (M+, 26), 203 (62), 201 (70), 94 (bp).

PREPARATION 9

2-fluoro-3-pyridin-4-ylbenzamide

To a mixture of 3-bromo-2-fluorobenzamide (1.2 g, 5.5 mmol), 1-pyridyl-4-boronic acid (0.74 g, 6.05 mmol) and sodium carbonate (0.98 g, 12.0 mmol) in toluene/ethanol (1:1, 60 ml) under nitrogen, was added palladium tetrakis (0.57 g, 10 mol %). The mixture was heated at reflux for 48 h, cooled to ambient temperature and after which water (50 ml) and ethylacetate (100 ml) was added. The organic layer was separated and the aqueous phase was extracted with ethylacetate (2×50 ml). The combined organic phases was evaporated to dryness and dissolved in aqueous hydrochloric acid (10%, 50 ml). The solution was washed with diethyl ether (2×40 ml), basified with sodium hydroxide (2 M) and extracted with ethylacetate (2×50 ml). The combined organic phases was dried (MgSO$_4$) and evaporated to dryness to give the title compound (0.47 g). MS m/z (rel. intensity, 70 eV) 216 (M+, 76), 200 (bp), 172 (20), 145 (18), 125 (19).

PREPARATION 10

3-(1-ethyl-1,2,3,6-tetrahydropyridin-4-yl)-2-fluorobenzamide

To neat 2-fluoro-3-pyridin-4-yl-benzamide (0.94 g, 4.34 mmol) was added 1-iodoethane (3 ml) and the resulting mixture was heated at 100° C. for 2 h. Excess 1-iodopropane was evaporated under reduced pressure and ethanol (40 ml) was added. The mixture was cooled to −20° C. and sodium borohydride (1.25 g, 34.8 mmol) was added in portions. The resulting mixture was stirred for 1 h, after which aqueous sodium carbonate (10%, 50 ml) was added. The aqueous phase was extracted with ethylacetate (3×100 ml) and the combined organic phases was dried (MgSO$_4$), filtered and evaporated to dryness. The residue was purified by flash column chromatography (ethylacetate/methanol, 1:1) to give the title compound (0.75 g). MS m/z (rel. intensity, 70 eV) 248 (M+, bp), 247 (37), 233 (99), 146 (22), 110 (41).

PREPARATION 11

3-(1-ethylpiperidin-4-yl)-2-fluorobenzamide

Preparation according to Example 2: 3-(1-ethyl-1,2,3,6-tetrahydropyridin-4-yl)-2-fluorobenzamide (0.75 g, 3.0 mmol), methanol (20 ml), palladium on carbon (0.2 g) and hydrochloric acid (0.2 ml, conc). Yield: 0.57 g. MS m/z (relative intensity, 70 eV) 250 (M+, 48), 249 (26), 236 (34), 235 (bp), 109 (30).

PREPARATION 12

4-(2,3-difluorophenyl)-1-propylpiperidin-4-ol

Preparation according to preparation 5: 1-bromo-2,3-difluorobenzene 5.0 g, 25.9 mmol), dry diethyl ether (100 ml), n-butyllithium (2.5 M in hexane, 11.4 ml, 28.5 mmol), 4-propyl-1-piperidone (3.65 g, 25.9 mmol). Yield: 6.43 g. MS m/z (rel. intensity, 70 eV) 255 (M+, 4), 226 (bp), 208 (32), 141 (17), 127 (16).

PREPARATION 13

4-(2,3-difluorophenyl)-1-propyl-1,2,3,6-tetrahydropyridine

Preparation according to preparation 4: 4-(2,3-difluorophenyl)-1-propylpiperidin-4-ol (6.43 g, 25.2 mmol), trifluoroacetic acid (40 ml). Yield: 3.35 g. MS m/z (rel. intensity, 70 eV) 237 (M+, 26), 209 (14), 208 (bp), 151 (20), 127 (23).

PREPARATION 14

4-(2,3-dichlorophenyl)pyridine

Preparation according to preparation 9: 1-bromo-2,3-dichlorobenzene (1.5 g, 6.6 mmol), toluene (30 ml), ethanol (30 ml), 1-pyridyl-4-boronic acid (1.0 g), sodium carbonate (1.4 g), palladium tetrakis (0.45 g). Yield: 1.0 g. MS m/z (rel. intensity, 70 eV) 225 (M+, 69), 223 (M+, bp), 188 (27), 153 (33), 126 (30).

PREPARATION 15

4-(2,3-dichlorophenyl)-1-propyl-1,2,3,6-tetrahydropyridine

Preparation according to preparation 10: 4-(2,3-dichlorophenyl)pyridine (1.0 g, 4.46 mmol), 1-iodopropane (6 ml), ethanol (60 ml), sodium borohydride (1.5 g, 44 mmol). Yield: 0.45 g. MS m/z (rel. intensity, 70 eV) 271 (M+, 16), 269 (M+, 28), 242 (62), 240 (bp), 127 (11).

PREPARATION 16 tert-butyl 4-(2,3-dichlorophenyl)-4-hydroxypiperidine-1-carboxylate

According to preparation 5: 1-Bromo-2,3-dichlorobenzene (1.0 g, 4.4 mmol), tetrahydrofurane (40 ml), n-butyllithium (2.5 M in hexane, 1.9 ml, 4.8 mmol), 4-boc-1-piperidone (0.9 g, 4.4 mmol). Yield: 0.7 g. MS m/z (relative intensity, 70 eV) 347 (M+, 1), 345 (M+, 2), 273 (17), 271 (24), 57 (bp).

PREPARATION 17

4-(2,3-dichlorophenyl)-1,2,3,6-tetrahydropyridine

According to Preparation 4: Tert-butyl-4-(2,3-dichlorophenyl)-4-hydroxypiperidine-1-carboxylate (3.0 g, 8.7 mmol), trifluoroacetic acid (30 ml). Yield: 0.88 g. MS m/z (rel. intensity, 70 eV) 229 (63), 228 (M+, 36), 227 (bp), 163 (53), 82 (85).

PREPARATION 18

4-(2,3-dichlorophenyl)piperidine

A mixture of 4-(2,3-dichlorophenyl)-1,2,3,6-tetrahydropyridine (0.49 g, 2.15 mmol), platinum oxide (0.11 g) and hydrochloric acid (0.1 ml, conc) in methanol (30 ml) was hydrogenated at 50 psi for 1 h under hydrogen gas. The reaction mixture was filtered through a pad of celite and the filtrate was concentrated and evaporated to dryness. Aqueous sodium carbonate (10%, 50 ml) was added. The aqueous phase was extracted with ethylacetate (3×30 ml) and the combined organic phases was dried ($MgSO_4$), filtered and evaporated to dryness. Yield: 0.17 g. MS m/z (rel. intensity, 70 eV) 230 (M+, 22), 229 (24), 228 (35), 196 (30), 194 (bp).

PREPARATION 19 tert-butyl 4-(2,3-difluorophenyl)-4-hydroxypiperidine-1-carboxylate

Preparation according to preparation 5: 1-Bromo-2,3-difluorobenzene (4.6 g, 23.8 mmol), tetrahydrofuran (50 ml), n-butyllithium (2.5 M in hexane, 10.5 ml, 26.25 mmol), 4-boc-1-piperidone (4.98 g, 24.0 mmol). Yield: 7.48 g. MS m/z (rel. intensity, 70 eV) 313 (M+, 2), 239 (36), 195 (22), 141 (22), 57 (bp).

PREPARATION 20

4-(2,3-difluorophenyl)-1,2,3,6-tetrahydropyridine

To a solution of tert-butyl-4-(2,3-difluorophenyl)-4-hydroxypiperidine-1-carboxylate (7.48 g, 23.9 mmol) in toluene (50 ml) was added sulfuric acid (18 M, 1.33 ml, 23.9 mmol) and the mixture was refluxed under a Dean-Stark water separator. The mixture was poured on to ice and was basified with aqueous sodium hydroxide solution (15%). The mixture was extracted with ethylacetate (3×50 ml) and the combined organic phases was dried ($MgSO_4$), filtered and evaporated to dryness. The residue was purified by flash column chromatography (MeOH) to give the title compound (2.5 g). MS m/z (rel. intensity, 70 eV) 195 (M+, bp), 194 (42), 166 (30), 151 (33), 127 (35).

PREPARATION 21

4-(2,3-difluorophenyl)piperidine

A mixture of 4-(2,3-difluorophenyl)-1,2,3,6-tetrahydropyridine (2.4 g, 12.3 mmol), palladium on active carbon (0.5 g) and formic acid (2.4 ml) in isopropanol (50 ml) was hydrogenated at 50 psi for 6 h under hydrogen gas. The reaction mixture was filtered through a pad of celite and the filtrate was concentrated and evaporated to dryness. Aqueous sodium carbonate (10%, 50 ml) was added. The aqueous phase was extracted with ethylacetate (3×60 ml) and the combined organic phases was dried ($MgSO_4$), filtered and evaporated to dryness. Yield: 2.11 g. MS m/z (rel. intensity, 70 eV) 197 (M+, bp), 196 (53), 140 (11), 127 (10), 114 (6).

PREPARATION 22

4-[2-fluoro-3-(trifluoromethyl)phenyl]-1-methylpiperidin-4-ol

Preparation according to preparation 5: 3-Bromo-2-fluorobenzotrifluoride (1.38 g, 5.68 mmol), tetrahydrofuran (50 ml), n-butyllithium (2.5 M in hexane, 2.3 ml, 5.68 mmol), 4-ethyl-1-piperidone (0.68 ml, 5.68 mmol). Yield: 1.25 g. MS m/z (rel. intensity, 70 eV) 277 (M+, bp), 276 (64), 260 (21), 259 (72), 258 (54).

PREPARATION 23

4-[2-fluoro-3-(trifluoromethyl)phenyl]-1-methyl-1,2,3,6-tetrahydropyridine

A solution of 4-[2-fluoro-3-(trifluoromethyl)phenyl]-1-methylpiperidin-4-ol (1.2 g, 4.33 mmol) in polyphosphoric acid (4 ml) was heated at 100° C. for 2 h. The mixture was poured on to ice and was basified with an aqueous sodium hydroxide solution (15%). The mixture was extracted with ethylacetate (3×50 ml) and the combined organic phases was dried (MgSO$_4$), filtered and evaporated to dryness. The residue was purified by flash column chromatography (ethylacetate/methanol, 1:1) to give the title compound (0.59 g). MS m/z (rel. intensity, 70 eV) 259 (M+, bp), 258 (66), 147 (74), 146 (27), 96 (52).

PREPARATION 24 tert-butyl 4-[2-fluoro-3-(trifluoromethoxy)phenyl]-4-hydroxypiperidine-1-carboxylate Preparation according to preparation 5: 1-fluoro-2-(trifluoromethoxy)benzene (10 g, 55.5 mmol), dry tetrahydrofurane (30 ml), lithium diisopropylamide (2 M in hexane, 31 ml, 62 mmol) and 4-boc-1-piperidone (13.3 g, 66.6 mmol). Yield: 11.5 g. MS m/z (rel. intensity, 70 eV) 379 (M+, 1), 306 (7), 305 (14), 261 (10), 57 (bp).

PREPARATION 25

4-[2-fluoro-3-(trifluoromethoxy)phenyl]-1,2,3,6-tetrahydropyridine

Preparation according to preparation 4: tert-butyl 4-[2-fluoro-3-(trifluoromethoxy) -phenyl]-4-hydroxypiperidine-1-carboxylate (11.5 g, 30.3 mmol), polyphosphoric acid (15 ml). Yield: 3.33 g. MS m/z (rel. intensity, 70 eV) 261 (M+, bp), 232 (17), 193 (24), 147 (64), 82 (86).

PREPARATION 26

4-[2-fluoro-3-(trifluoromethoxy)phenyl]piperidine

Preparation according to Example 2: 4-[2-fluoro-3-(trifluoromethoxy)phenyl]-1,2,3,6-tetrahydropyridine (3.33 g, 12.7 mmol), palladium on carbon (0.35 g), hydrochloric acid (0.5 ml, conc), methanol (30 ml). Yield: 2.68 g. MS m/z (relative intensity, 70 eV) 263 (M+, 39), 262 (27), 206 (8), 178 (7) 56 (bp).

PREPARATION 27

1-(benzyloxy)-3-bromo-2-fluorobenzene

To a solution of 3-bromo-2-fluorophenol (1.8 g, 9.42 mmol) in acetone (25 ml) was added sodium carbonate (2.55 g, 20 mmol) and the mixture was stirred for 5 min. Benzylbromide (1.2 ml, 10.3 mmol) was added and the reaction mixture was heated at reflux for 20 h. Water (50 ml) and ethyl acetate (50 ml) was added and the phases were separated. The aqueous phase was extracted with ethyl acetate (2×50 ml) and the combined organic phases was dried (MgSO4) and evaporated under reduced pressure to give an oil. The residue was purified by flash column chromatography (isooctane/ethyl acetate, 5:1) to give the title compound (2.8 g). MS m/z (rel. intensity, 70 eV) 282 (M+, 2), 280 (M+, 2), 163 (2), 161 (2), 91 (bp).

PREPARATION 28

4-[3-(benzyloxy)-2-fluorophenyl]-1-ethylpiperidin-4-ol

Preparation according to preparation 5: 1-(benzyloxy)-3-bromo-2-fluorobenzene (2.8 g, 9.96 mmol), dry diethyl ether (100 ml), n-butyllithium (2.5 M in hexane, 5.2 ml, 9.9 mmol), 4-ethyl-1-piperidone (1.5 ml, 10.9 mmol). Yield: 2.1 g. MS m/z (rel. intensity, 70 eV) 329 (M+, 30), 314 (56), 296 (20), 238 (59), 91 (bp).

PREPARATION 29

3-(1-ethyl-1,2,3,6-tetrahydropyridin-4-yl)-2-fluorophenol

Preparation according to preparation 4: 4-[3-(benzyloxy)-2-fluorophenyl]-1-ethylpiperidin-4-ol (1.9 g, 5.77 mmol), trifluoroacetic acid (5 ml). Yield: 1.1 g. MS m/z (rel. intensity, 70 eV) 221 (M+, bp), 220 (43), 206 (95), 163 (10), 110 (14).

PREPARATION 30

3-(1-ethylpiperidin-4-yl)-2-fluorophenol

Preparation according to Example 2: 3-(1-ethyl-1,2,3,6-tetrahydropyridin-4-yl)-2-fluorophenol (1.1 g, 4.97 mmol), methanol (20 ml), palladium on carbon (0.26 g) and hydrochloric acid (0.2 ml, conc). Yield: 1.1 g. MS m/z (relative intensity, 70 eV) 223 (M+, 32), 222 (17), 209 (13), 208 (bp) 84 (20).

PREPARATION 31 tert-butyl 4-[2-fluoro-3-(trifluoromethyl)phenyl]-4-hydroxypiperidine-1-carboxylate Preparation according to preparation 5: 1-bromo-2-fluoro-3-(trifluoromethyl)benzene (8.0 g, 32.9 mmol), dry diethyl ether (100 ml), n-butyllithium (2.5 M in hexane, 13 ml, 32.9 mmol), 4-boc-1-piperidone (7.8 g, 39.5 mmol). Yield: 8.5 g. MS m/z (rel. intensity, 70 eV) 363 (M+, 2), 289 (44), 245 (28), 191 (23), 57 (bp).

The following tests were used for evaluation of the compounds according to the invention.

In Vivo Test: Behaviour

Behavioural activity was measured using eight Digiscan activity monitors (RXYZM (16) TAO, Omnitech Electronics, Columbus, Ohio, USA), connected to an Omnitech Digiscan analyzer and an Apple Macintosh computer equipped with a digital interface board (NB DIO-24, National Instruments, USA). Each activity monitor consisted of a quadratic metal frame (W×L=40 cm×40 cm) equipped with photobeam sensors. During measurements of behavioural activity, a rat was put in a transparent acrylic cage (W×L×H, 40×40×30 cm) which in turn was placed in the activity monitor. Each activity monitor was equipped with three rows of infrared photobeam sensors, each row consisting of 16 sensors. Two rows were placed along the front and the side of the floor of the cage, at a 90° angle, and the third row was placed 10 cm above the floor to measure vertical activity. Photobeam sensors were spaced 2.5 cm apart. Each activity monitor was fitted in an identical sound and light attenuating box containing a weak house light and a fan.

The computer software was written using object oriented programming (LabVIEW®, National instruments, Austin, Tex., USA).

Behavioural data from each activity monitor, representing the position (horisontal center of gravity and vertical activity) of the animal at each time, were recorded at a sampling frequency of 25 Hz and collected using a custom written LABView™ application. The data from each recording session were stored and analyzed with respect to distance traveled. Each behavioural recording session lasted 60 min, starting approximately 4 min after the injection of test compound. Similar behavioural recording procedures were applied for drug-naïve and drug pre-treated rats. Rats pretreated with d-amphetamine were given a dose of 1.5 mg/kg i.p. 10 min before the recording session in the activity monitor. Rats pretreated with MK-801 were given a dose of 0.7 mg/kg i.p. 90 min before the recording session in the activity monitor. The results are presented as counts/60 minutes, or counts/30 minutes, in arbitrary length units. Statistical comparisons were carried out using Student's t-test against the control group. In MK-801 or amphetamine pre-treated animals, statistical comparisons were made against the MK801 or d-amphetamine controls, respectively.

$ED_{50}$ values for reduction of amphetamine-induced hyperlocomotion are calculated by curve fitting. For most compounds, the evaluation is based on 16 amphetamine pretreated animals over the dose range 0, 11, 33 and 100 μmol/kg s.c. in one single experiment, with complementary doses in separate experiments. Calculations are based on distance during the last 45 minutes of one hour of measurement. The distances are normalised to amphetamine-control and fitted by least square minimization to the function "End-(End-Control)/(1+(dose/$ED_{50}$)$^{Slope}$)". The four parameters are fitted with the restrictions: $ED_{50}>0$, $0.5<Slope<3$, $End>0\%$ of control. To estimate confidence levels for the parameters, the fit is repeated 100 times with a random evenly distributed squared weight (0 to 1) for every measurement value. Presented $ED_{50}$-ranges cover 95% of these values.

In Vivo Test: Neurochemistry

After the behavioural activity sessions, the rats were decapitated and their brains rapidly taken out and put on an ice-cold petri-dish. The limbic forebrain, the striatum, the frontal cortex and the remaining hemispheral parts of each rat were dissected and frozen. Each brain part was subsequently analyzed with respect to its content of monoamines and their metabolites.

The monoamine transmitter substances (NA (noradrenaline), DA (dopamine), 5-HT (serotonin)) as well as their amine (NM (normethanephrine), 3-MT (3-methoxytyramine)) and acid (DOPAC (3,4-dihydroxyphenylacetic acid), 5-HIAA (5-hydroxyindoleacetic acid), HVA (homovanillic acid)) metabolites are quantified in brain tissue homogenates by HPLC separations and electrochemical detection The analytical method is based on two chromatographic separations dedicated for amines or acids. Two chromatographic systems share a common auto injector with a 10-port valve and two sample loops for simultaneous injection on the two systems. Both systems are equipped with a reverse phase column (Luna C18(2), dp 3 μm, 50*2 mm i.d., Phenomenex) and electrochemical detection is accomplished at two potentials on glassy carbon electrodes (MF-1000, Bioanalytical Systems, Inc.). The column effluent is passed via a T-connection to the detection cell or to a waste outlet. This is accomplished by two solenoid valves, which block either the waste or detector outlet. By preventing the chromatographic front from reaching the detector, better detection conditions are achieved. The aqueous mobile phase (0.4 ml/min) for the acid system contains citric acid 14 mM, sodium citrate 10 mM, MeOH 15% (v/v) and EDTA 0.1 mM. Detection potentials relative to Ag/AgCl reference are 0.45 and 0.60V. The aqueous ion pairing mobile phase (0.5 ml/min) for the amine system contains citric acid 5 mM, sodium citrate 10 mM, MeOH 9% (v/v), MeCN 10.5% (v/v), decane sulfonic acid 0.45 mM, and EDTA 0.1 mM. Detection potentials relative to Ag/AgCl reference are 0.45 and 0.65V.

$ED_{50}$ values for the increase of DOPAC in striatum are calculated by curve fitting. For most compounds, the evaluation is based on 20 animals over the dose range 0, 3.7, 11, 33 and 100 μmol/kg s.c. in one single experiment. The DOPAC levels are normalised to control and fitted by least square minimization to the function "End-(End-Control)/(1+(dose/$ED_{50}$)$^{Slope}$)". The four parameters are fitted with the restrictions: $ED_{50}>0$, $0.5<Slope<3$, $350<End<400$ or $End=200\%$ of control (see table 1). To estimate confidence levels for the parameters, the fit is repeated 100 times with a random evenly distributed squared weight (0 to 1) for every measurement value. Presented $ED_{50}$-ranges cover 95% of these values.

Microdialysis

Male Sprague-Dawley rats weighing 220-320 g were used throughout the experiments. Before the experiment the animals were group housed, five animals in each cage, with free access to water and food. The animals were housed at least one week after arrival prior to surgery and use in the experiments. Each rat was used only once for microdialysis.

We use a modified version (Waters, Lofberg et al. 1994) of the I-shaped probe (Santiago and Westerink 1990). The dialysis membrane we use is the AN69 polyacrylonitrile/sodium methalylsulfonate copolymer (HOSPITAL; o.d./i.d. 310/220 μm: Gambro, Lund, Sweden). In the dorsal striatum we use probes with an exposed length of 3 mm of dialysis membrane and in the prefrontal cortex the corresponding length is 2.5 mm. The rats were operated under isoflurane inhalation anesthesia while mounted into a Kopf stereotaxic instrument. Coordinates were calculated relative to bregma; dorsal striatum AP+1, ML±2.6, DV−6.3; Pf cortex, AP+3.2, 8° ML±1.2, DV−4.0 according to (Paxinos and Watson 1986). The dialysis probe was positioned in a burr hole under stereotaxic guidance and cemented with phosphatine dental cement.

The rats were housed individually in cages for 48 h before the dialysis experiments, allowing them to recover from surgery and minimizing the risk of drug interactions with the anaesthetic during the following experiments. During this period the rats had free access to food and water. On the day of experiment the rats were connected to a micro perfusion pump via a swivel and were replaced in the cage where they could move freely within its confinements. The perfusion medium was a Ringer's solution containing in mmol/l: NaCl; 140, CaCl2; 1.2, KCl; 3.0, MgCl2; 1.0 and ascorbic acid; 0.04 according to (Moghaddam and Bunney 1989). The pump was set to a perfusion speed of 2 μl/min and 40 μl samples were collected every 20 min.

30 μl of each sample was injected into the chromatograph. On a 10-port injector (Valco CLOW), with two sample loops mounted in series (2 μl and 20 μl), each brain dialysate sample is loaded in both loops simultaneously. When the valve is switched to inject the main part of the 20 μl sample is introduced into a reverse-phase ion-pairing system for dopamine (DA), norepinephrine (NA), normetanephrine (NM), 3-methoxytyramine(3-MT) and serotonin (5-hydroxytryptamine, 5-HT) determination (large loop), while a small fraction (2 μl, from the small loop) is introduced on a reverse-phase column for the chromatography of the acidic monoamine metabolites 3,4-di-hydroxyphenylacetic acid (DOPAC), homovanillic acid (HVA) and 5-hydroxyindoleacetic acid (5-HIAA). The currents generated by the two EC detectors are converted to digital data and evaluated using Chromelion software (Dionex, Sunnyvale, Calif.) on a PC. The method sample turn over time was 4.5 min and two parallel experiments are normally analysed simultaneously on the system. After the experiment the rats were uncoupled from the perfusion pump and decapitated. Their brains were rapidly taken out and fixed in Neo-fix solution (Kebo-lab, Sweden) for subsequent inspection of probe localisation. The Animal Ethics Committee in Göteborg, Sweden approved the procedures applied in these experiments.

Moghaddam, B. and B. S. Bunney (1989). "Ionic Composition of Microdialysis Perfusing Solution Alters the Pharmacological Responsiveness and Basal Outflow of Striatal Dopamine." J. Neurochem. 53: 652-654.

Paxinos, G. and C. Watson (1986). The Rat Brain in Stereotaxic Coordinates. New York, Academic Press.

Santiago, M. and B. H. C. Westerink (1990). "Characterization of the in vivo release of dopamine as recorded by different types of intracerebral microdialysis probes." Naunyn-Schmiedeberg's Arch. Pharmacol. 342: 407-414.

Waters, N., L. Lofberg, S. Haadsma-Svensson, K. Svensson, C. Sonesson and A. Carlsson (1994). "Differential effects of dopamine D2 and D3 receptor antagonists in regard to dopamine release, in vivo receptor displacement and behaviour." J Neural Transm Gen Sect 98(1): 39-55.

In Vivo Test: Oral Bioavailability

Experiments are performed 24 hours after implantation of arterial and venous catheters. Test compound is administered orally at 12.5 µmol/kg or intravenously at 5 µmol/kg using the venous catheters, n=3 per group. Arterial blood samples are then taken during six hours at 0, 3, 9, 27, 60, 120, 180, 240, 300 and, 360 minutes after administration of the test compound. The oral bioavailability was calculated as the ratio of the AUC (Area under curve) obtained after oral administration over the AUC obtained after intravenous administration for each rat. The parameter AUC was calculated according to the following:

AUC: the area under the plasma concentration versus time curve from time zero to the last concentration measured (Clast), calculated by the log/linear trapezoidal method.

The levels of test compound are measured by means of liquid chromatography-mass spectrometry (LC-MS) (Hewlett-Packard 1100MSD Series). The LC-MS module includes a quaternary pump system, vacuum degasser, thermostatted autosampler, thermostatted column compartment, diode array detector and API-ES spray chamber. Data handling was performed with a HP ChemStation rev.A.06.03. system. Instrument settings:MSD mode: Selected ion monitoring (SIM) MSD polarity: Positive Gas temp: 350° C. Drying gas: 13.0 l/min Nebulizer gas: 50 psig Capillary voltage: 5000 V Fragmentor voltage: 70 V Analytical column: Zorbax eclipse XDB-C8 (4.6*150 mm, 5 µm) at 20° C. The mobile phase was acetic acid (0.03%) (solvent A) and acetonitrile (solvent B). The flow rate of the mobile phase was 0.8 ml/min. The elution was starting at 12% of solvent B isocratic for 4.5 min, then increasing linearity to 60% over 4.5 min.

Extractions procedure: Plasma samples (0.25-0.5 ml) were diluted with water to 1 ml, and 60 pmol (100 µl) internal standard (−)-OSU6241 was added. The pH was adjusted to 11 by the addition of 25 µl saturated $Na_2CO_3$. After mixing, the samples were extracted with 4 ml dichloromethane by shaking for 20 min. The organic layer was after centrifugation transferred to a smaller tube and evaporated to dryness under a stream of nitrogen. The residue was then dissolved in 120 µl mobile phase (acetic acid (0.03%): acetonitrile, 95:5) for LC-MS analysis (10 µl injected). The selective ion ($MH^+$) was monitored for each Example, and $MH^+$ 296 for (−)-OSU6241 ((3-[3-(ethylsulfonyl)phenyl]-1-propylpiperidine). A standard curve over the range of 1-500 pmol is prepared by adding appropriate amounts of test compound to blank plasma samples.

In Vitro Test: Metabolic Stability in Rat Liver Microsomes

Rat liver microsomes were isolated as described by Förlin (1980) Tox Appl Pharm. 54(3) 420-430, with minor modifications e.g. 3 mL/g liver of a 0.1 M $Na/K*PO_4$ buffer with 0.15M KCl, pH 7.4, (buffer 1) was added before homogenisation, the homogenate was centrifuged for 20 minutes instead of 15, the supernatant was ultracentrifuged at 100.000 g instead of 105.000 g and the pellet from the ultracentrifugation was resuspended in 1 mL/g liver of 20% v/v 87% glycerol in buffer 1.

1 µL of, 0.2 or 1 mM test substance diluted in water, and 10 µL 20 mg/mL rat liver microsome were mixed with 149 µL 37° C. buffer 1 and the reaction was started by addition of 40 µL 4.1 mg/mL NADPH. After 0 or 15 minutes incubation at 37° C. in a heating block (LAB-LINE, MULTI-BLOK Heater or lab4you, TS-100 Thermo shaker at 700 rpm) the reaction was stopped by addition of 100 µL pure acetonitrile. The protein precipitation was then removed by rejecting the pellet after centrifugation at 10.000 g for 10 minutes (Heraeus, Biofuge fresco) in 4° C. The test compound was analysed using HPLC-MS (Hewlett-Packard 1100MSD Series) with a Zorbax SB-C18 column (2.1*150 mm, 5 µm) using 0.03% formic acid and acetonitrile as mobile phase (gradient) or a Zorbax Eclipse XDB-C18 (3*75 mm, 3.5 µm) using 0.03% acetic acid and acetonitrile as mobile phase (gradient). The 15 min turnover was calculated as the fraction of test compound eliminated after 15 minutes, expressed in percent of 0 min levels, i.e. 100*[conc test compound at 0 min−concentration at 15 min]/conc at 0 min.

Preparation of liver microsomes was performed as described in Förlin (1980). Protocols for incubation with liver microsomes are referred in Crespi et Stresser (2000), and Renwick et al (2001).

REFERENCES

Crespi C L, and D M Stressser (2000). Fluorometric screening for metabolism based drug-drug interactions. J. Pharm. Tox. Meth. 44. 325-331

Förlin L. (1980) Effects of Clophen A50, 3-methylcholantrene, pregnenolone-16aq -carbonitrile and Phenobarbital on the hepatic microsomal cytochrome P-450-dependent monooxygenaser system in rainbow trout, salmo gairdneri, of different age and sex. Tox Appl Pharm. 54(3) 420-430

Renwick, A B et al. (2001).Metabolism of 2,5-bis(trifluoromethyl)-7-benzyloxy-4-trifluoromethylcoumarin by human hepatic CYP isoforms: evidence for selectivity towards CYP3A4. Xenobiotica 31(4): 187-204

The invention claimed is:

1. A compound of Formula 1:

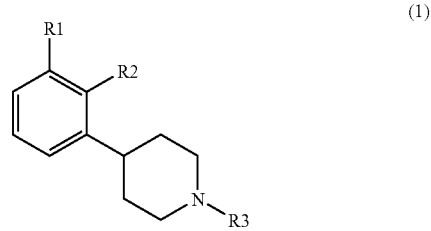

(1)

wherein:

$R_1$ is selected from the group consisting of —CN, —$OCF_3$, —$OCHF_2$, —$SCF_3$, —$SCHF_2$, —$CF_3$, F, Cl, —$CH_3$ and —$OCH_3$;

$R_2$ is selected from the group consisting of F, Cl, Br, and $CH_3$;

$R_3$ is selected from the group consisting of $C_1$-$C_3$ alkyls and allyl, provided that when $R_1$ is CN or $CF_3$, $R_3$ can only be $C_1$-$C_2$ alkyls;
and the pharmaceutically acceptable salts thereof.

2. A compound according to claim 1, wherein $R_1$ is selected from the group consisting of, CN, $CF_3$, Cl and F.

3. A compound according to claim 1, wherein $R_1$ is selected from the group consisting of F, $C_1$ and $CF_3$.

4. A compound according to claim 1, wherein $R_2$ is selected from the group consisting of F and Cl.

5. A compound according to claim 1, wherein $R_2$ is F and $R_3$ is selected from the group consisting of n-propyl, and ethyl.

6. A compound according to claim 1, selected from the group consisting of
    4-(3-fluoro-2-methylphenyl)-1-propylpiperidine
    1-ethyl-4-(3-fluoro-2-methylphenyl)piperidine
    1-allyl-4-(3-fluoro-2-methylphenyl)piperidine
    4-(2,3-difluorophenyl)-1-propylpiperidine
    4-(2,3-difluorophenyl)-1-ethylpiperidine
    1-allyl-4-(2,3-difluorophenyl)piperidine
    4-(2-chloro-3-fluorophenyl)-1-propylpiperidine
    4-(2-chloro-3-fluorophenyl)-1-ethylpiperidine
    1-allyl-4-(2-chloro-3-fluorophenyl)piperidine
    1-ethyl-4-[2-methyl-3-(trifluoromethyl)phenyl]piperidine
    1-ethyl-4-[2-fluoro-3-(trifluoromethyl)phenyl]piperidine
    4-[2-chloro-3-(trifluoromethyl)phenyl]-1-ethylpiperidine
    4-(3-chloro-2-methylphenyl)-1-propylpiperidine
    4-(3-chloro-2-methylphenyl)-1-ethylpiperidine
    1-allyl-4-(3-chloro-2-methylphenyl)piperidine
    4-(3-chloro-2-fluorophenyl)-1-propylpiperidine
    4-(3-chloro-2-fluorophenyl)-1-ethylpiperidine
    1-allyl-4-(3-chloro-2-fluorophenyl)piperidine
    4-(2,3-dichlorophenyl)-1-propylpiperidine
    4-(2,3-dichlorophenyl)-1-ethylpiperidine
    1-allyl-4-(2,3-dichlorophenyl)piperidine
    4-[3-(difluoromethoxy)-2-methylphenyl]-1-propylpiperidine
    4-[3-(difluoromethoxy)-2-methylphenyl]-1-ethylpiperidine
    1-allyl-4-[3-(difluoromethoxy)-2-methylphenyl]piperidine
    4-[3-(difluoromethoxy)-2-fluorophenyl]-1-propylpiperidine
    4-[3-(difluoromethoxy)-2-fluorophenyl]-1-ethylpiperidine
    1-allyl-4-[3-(difluoromethoxy)-2-fluorophenyl]piperidine
    4-[2-chloro-3-(difluoromethoxy)phenyl]-1-propylpiperidine
    4-[2-chloro-3-(difluoromethoxy)phenyl]-1-ethylpiperidine
    1-allyl-4-[2-chloro-3-(difluoromethoxy)phenyl]piperidine
    4-[2-methyl-3-(trifluoromethoxy)phenyl]-1-propylpiperidine
    1-ethyl-4-[2-methyl-3-(trifluoromethoxy)phenyl]piperidine
    1-allyl-4-[2-methyl-3-(trifluoromethoxy)phenyl]piperidine
    4-[2-fluoro-3-(trifluoromethoxy)phenyl]-1-propylpiperidine
    1-ethyl-4-[2-fluoro-3-(trifluoromethoxy)phenyl]piperidine
    1-allyl-4-[2-fluoro-3-(trifluoromethoxy)phenyl]piperidine
    4-[2-chloro-3-(trifluoromethoxy)phenyl]-1-propylpiperidine
    4-[2-chloro-3-(trifluoromethoxy)phenyl]-1-ethylpiperidine
    1-allyl-4-[2-chloro-3-(trifluoromethoxy)phenyl]piperidine
    3-(1-ethylpiperidin-4-yl)-2-methylbenzonitrile
    3-(1-ethylpiperidin-4-yl)-2-fluorobenzonitrile
    2-chloro-3-(1-ethylpiperidin-4-yl)benzonitrile
    4-[2-fluoro-3-(trifluoromethyl)phenyl]-1-methylpiperidine
    2-chloro-3-(1-methylpiperidin-4-yl)benzonitrile
    4-[2-chloro-3-(trifluoromethyl)phenyl]-1-methylpiperidine
    2-fluoro-3-(1-methylpiperidin-4-yl)benzonitrile.

7. A compound according to claim 1, selected from the group consisting of
    4-(2,3-difluorophenyl)-1-propylpiperidine
    4-(2,3-difluorophenyl)-1-ethylpiperidine
    1-allyl-4-(2,3-difluorophenyl)piperidine
    4-(2-chloro-3-fluorophenyl)-1-propylpiperidine
    4-(2-chloro-3-fluorophenyl)-1-ethylpiperidine
    1-allyl-4-(2-chloro-3-fluorophenyl)piperidine
    4-[2-chloro-3-(trifluoromethyl)phenyl]-1-ethylpiperidine
    4-(3-chloro-2-fluorophenyl)-1-propylpiperidine
    4-(3-chloro-2-fluorophenyl)-1-ethylpiperidine
    1-allyl-4-(3-chloro-2-fluorophenyl)piperidine
    4-(2,3-dichlorophenyl)-1-propylpiperidine
    4-(2,3-dichlorophenyl)-1-ethylpiperidine
    1-allyl-4-(2,3-dichlorophenyl)piperidine
    4-[3-(difluoromethoxy)-2-fluorophenyl]-1-propylpiperidine
    4-[3-(difluoromethoxy)-2-fluorophenyl]-1-ethylpiperidine
    1-allyl-4-[3-(difluoromethoxy)-2-fluorophenyl]piperidine
    4-[2-chloro-3-(difluoromethoxy)phenyl]-1-propylpiperidine
    4-[2-chloro-3-(difluoromethoxy)phenyl]-1-ethylpiperidine
    1-allyl-4-[2-chloro-3-(difluoromethoxy)phenyl]piperidine
    4-[2-fluoro-3-(trifluoromethoxy)phenyl]-1-propylpiperidine
    1-ethyl-4-[2-fluoro-3-(trifluoromethoxy)phenyl]piperidine
    1-allyl-4-[2-fluoro-3-(trifluoromethoxy)phenyl]piperidine
    4-[2-chloro-3-(trifluoromethoxy)phenyl]-1-propylpiperidine
    4-[2-chloro-3-(trifluoromethoxy)phenyl]-1-ethylpiperidine
    1-allyl-4-[2-chloro-3-(trifluoromethoxy)phenyl]piperidine
    3-(1-ethylpiperidin-4-yl)-2-fluorobenzonitrile
    2-chloro-3-(1-ethylpiperidin-4-yl)benzonitrile
    4-[2-fluoro-3-(trifluoromethyl)phenyl]-1-methylpiperidine
    2-chloro-3-(1-methylpiperidin-4-yl)benzonitrile
    4-[2-chloro-3-(trifluoromethyl)phenyl]-1-methylpiperidine
    2-fluoro-3-(1-methylpiperidin-4-yl)benzonitrile.

8. A pharmaceutical composition comprising a compound according to claim 1 and one or more pharmaceutically acceptable carriers or diluents.

* * * * *